United States Patent

Tsuchiya et al.

[11] Patent Number: 6,040,449
[45] Date of Patent: Mar. 21, 2000

[54] FLUORINE-CONTAINING 1, 4-DISUBSTITUTED PIPERIDINE DERIVATIVES

[75] Inventors: Yoshimi Tsuchiya, Tsukuba; Takashi Nomoto, Menuma-machi; Hirokazu Ohsawa, Tsukuba; Kumiko Kawakami, Tsukuba; Kenji Ohwaki, Tsukuba; Masaru Nishikibe, Tsukuba, all of Japan

[73] Assignee: Banyu Pharmaceutical Co Ltd, Tokyo, Japan

[21] Appl. No.: 09/290,607

[22] Filed: Apr. 13, 1999

Related U.S. Application Data

[62] Division of application No. 08/903,768, Jul. 31, 1997, Pat. No. 5,948,792.

[30] Foreign Application Priority Data

Aug. 1, 1996 [JP] Japan ................................ 8-219436
Feb. 21, 1997 [JP] Japan ................................ 9-53979

[51] Int. Cl.⁷ ........................................... C07D 401/06
[52] U.S. Cl. ..................................................... 546/193
[58] Field of Search ............................................. 546/193

[56] References Cited

U.S. PATENT DOCUMENTS

| 5,621,010 | 4/1997 | Sueda et al. ........................ 514/596 |
| 5,750,540 | 5/1998 | Tsuchiya et al. .................... 514/318 |

FOREIGN PATENT DOCUMENTS

| 309424A | 3/1989 | European Pat. Off. . |
| 733621A1 | 9/1996 | European Pat. Off. . |
| 751127 | 1/1997 | European Pat. Off. . |
| 5283763 | 7/1977 | Japan . |
| 5679688 | 6/1981 | Japan . |
| 07258250 | 10/1995 | Japan . |
| 9005133 | 5/1990 | WIPO . |
| 9713766 | 4/1997 | WIPO . |

OTHER PUBLICATIONS

Japanese language publication "Seitai no Kagaku" (biochemistry), vol. 42(5), p. 380–385, 1991 and partial English translation.

Chem. Pharm. Bull., vol. 32, No. 3, (1984), SUGAI, Saburo, et al., "Studies on Spasmolytics I. Synthesis and Spasmolytic . . . piperidines", p. 967–976.

Chem. Pharm. Bull., vol. 32, No. 3, (1984), SUGAI, Saburo, et al., "Studies on Spasmolytics. II. Synthesis . . . Compounds", p. 997–985.

Chem. Pharm. Bull. vol. 32, No. 3, (1984), SUGAI, Saburo, et al., "Studies on Spasmolytics. III. Synthesis . . . Salts", p. 1126–1134.

Chem. Pharm. Bull. vol. 33, No. 2, (1985), Yoshida, Seiichiro, et al., "Structure–Activity Relationship . . . piperidine Deriviatives", p. 818–822.

*Primary Examiner*—Ceila Chang

[57] ABSTRACT

In the production of fluorine-containing 1,4-disubstituted piperidine derivatives by the reaction of a carboxylic acid of formula

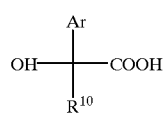

where Ar represents aryl or heteroaryl and $R^{10}$ represents $C_3$–$C_6$ cycloalkyl in which up to 4 hydrogen atoms are substituted with fluorine or $C_3$–$C_6$ cycloalkyl having 1 to 2 protected or unprotected hydroxyl or oxo groups, or a reactive derivative thereof, with a piperidine derivative of formula [IV] as defined in the specification, especially useful results are obtained using 4-amino-1-(6-aminopyridin-2-ylmethyl)piperidine or a salt thereof, e.g., trihydrochloride, as the piperidine derivative.

2 Claims, No Drawings

FLUORINE-CONTAINING 1, 4-DISUBSTITUTED PIPERIDINE DERIVATIVES

This application is a divisional of Ser. No. 09/903,768 filed Jul. 31, 1997, now U.S. Pat. No. 5,948,792.

TECHNICAL FIELD

This invention relates to novel fluorine-containing 1,4-disubstituted piperidine derivatives, processes for preparing them, pharmaceutics containing them and their use as medicines, especially in the treatment or prophylaxis of various diseases of the respiratory, urinary and digestive systems.

BACKGROUND ART

Antagonism to muscarinic receptors are known to cause bronchodilation, gastrointestinal hypanakinesis, gastric hyposecretion, dry mouth, mydriasis, suppression of bladder contraction, hypohidrosis, tachycardia and the like ["Basic and Clinical Pharmacology", 4th ed., APPLETON & LANGE, pp. 83–92 (1989); Drug News & Perspective, 5(6), pp. 345–352 (1992)].

It has been made clear through recent studies that there are at least three subtypes of muscarinic receptors; the $M_1$ receptors being present mainly in the brain, the $M_2$ receptors mainly in the heart, and the $M_3$ receptors, on smooth muscles and glandular tissues. Whereas, all of the large number of compounds heretofore known to exhibit antagonism to muscarinic receptors non-selectively antagonize the three subtypes of muscarinic receptors. Consequently, attempts to use these compounds as therapeutic or prophylactic agents for diseases of the respiratory system have caused undesirable side effects such as dry mouth, nausea and mydriasis. Still in addition, particularly serious side effects associated with the central nervous system, such as dementia, attributable to the $M_1$ receptors and those associated with the heart, such as tachycardia mediated by the $M_2$ receptors pose problems and their solution is strongly demanded.

We have disclosed, as a drug meeting the demand, 1,4-disubstituted piperidine derivatives (see: PCT WO96/33973). However, creation of even more excellent drug has been in demand.

An object of the present invention is to create even a better drug than said known compounds, whereby to provide pharmaceutics exhibiting highly selective antagonism to $M_3$ receptors and minimizing adverse side effect and which, therefore, provide safe and effective pharmaceutics for treatment or prophylaxis of diseases associated with muscarine $M_3$ receptors, eg., such respiratory diseases as chronic obstructive pulmonary diseases, chronic bronchitis, asthma and rhinitis; digestive diseases such as irritable bowel syndrome, convulsive colitis, diverticulitis and pain accompanying contraction of smooth muscles of the digestive system; urinary disorders like urinary incontinence and frequency in neurogenic pollakiurea, neurogenic bladder, nocturnal enuresis, unstable bladder, cystospasm and chronic cystisis; and motion sickness.

DISCLOSURE OF THE INVENTION

According to the present invention, there are provided novel fluorine-containing 1,4-disubstituted piperidine derivatives of the general formula [I]

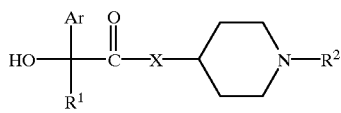

and pharmaceutically acceptable salts thereof, wherein:

Ar represents an aryl group or a heteroaryl group having 1 to 2 hetero atoms selected from a group consisting of nitrogen, oxygen and sulfur (any 1 to 3 hydrogen atoms on the ring of said aryl or heteroaryl group may be substituted with lower alkyl, trifluoromethyl, cyano, hydroxyl, nitro, lower alkoxycarbonyl, halogen, lower alkoxy, amino or lower alkylamino);

$R^1$ represents $C_3$–$C_6$ cycloalkyl whose any 1–4 hydrogen atoms may be substituted with fluorine atoms(s);

$R^2$ represents $C_5$–$C_{15}$ saturated or unsaturated aliphatic hydrocarbon groups whose any 1 to 6 hydrogen atoms may be substituted with fluorine atom(s), aralkyl, arylalkenyl, heteroarylalkyl or heteroarylalkenyl group having 1 to 2 hetero atoms selected from a group consisting of nitrogen, oxygen and sulfur (optionally any 1 to 3 hydrogen atoms on the ring in said aralkyl, arylalkenyl, heteroarylalkyl or heteroarylalkenyl group may be substituted with lower alkyl, trifluoromethyl, cyano, hydroxyl, nitro, lower alkoxycarbonyl, halogen, lower alkoxy, amino or lower alkylamino); and X stands for O or NH.

provided that at least either one of $R^1$ and $R^2$ contains one or more fluorine atoms.

The compounds of the above formula [I] which are provided by the present invention have not only potent and selective antagonistic activity for muscarinic $M_3$ receptors but also little side effect. Furthermore they exhibit excellent oral activity, duration of action and pharmacokinetics. Hence, they are very useful in the treatment or prophylaxis of diseases such respiratory diseases as chronic obstructive pulmonary diseases, chronic bronchitis, asthma and rhinitis: digestive diseases such as irritable bowel syndrome, convulsive colitis, diverticulitis and pain accompanying contraction of smooth muscles of the digestive system: urinary disorders like urinary incontinence and frequency in neurogenic pollakiurea, neurogenic bladder, nocturnal enuresis, unstable bladder, cystospasm and chronic cystisis: and motion sickness.

Hereinafter the meaning of the technical terms used in the present specification are elucidated and the invention is explained in further details.

"An aryl group (any 1 to 3 hydrogen atoms on the ring in said aryl group may be substituted with lower alkyl, trifluoromethyl, cyano, hydroxyl, nitro, lower alkoxycarbonyl, halogen, lower alkoxy, amino or lower alkylamino)" signifies a substituted or unsubstituted $C_6$–$C_{11}$ aryl group, examples of which including unsubstituted phenyl group, naphthyl group or those containing the above-named substituent(s).

As examples of "a heteroaryl group having 1–2 hetero atoms selected from a group consisting of nitrogen, oxygen and sulfur (any 1 to 3 hydrogen atoms on the ring of said heteroaryl group may be substituted with lower alkyl, trifluoromethyl, cyano, hydroxyl, nitro, lower alkoxycarbonyl, halogen, lower alkoxy, amino or lower alkylamino)", unsubstituted 2-pyridyl, 3-pyridyl, 4-pyridyl, 2-thiazolyl, 4-thiazolyl, 2-thienyl, 3-thienyl, 1-imidazolyl, 2-imidazolyl, 4-imidazolyl, 3-pyrazolyl, 4-pyrazolyl, 2-furyl, 3-furyl, 2-pyrrolyl, 3-pyrrolyl, 2-pyrimidinyl, 4-pyrimidinyl, 5-pyrimidinyl, 2-pyrazinyl, 3-pyridazinyl, 4-pyridazinyl, 2-quinolinyl, 2-benzothienyl and 2-indolyl group; and those which are substituted with the above-named substituents can be named.

Also examples of "$C_3$–$C_6$ cycloalkyl whose 1–4 hydrogen atoms may be substituted with fluorine atom(s)" include: cyclopropyl, cyclobutyl, cyclopentyl, cyclohexyl, 1-fluorocyclopropyl, 1-fluorocyclobutyl, 1-fluorocyclopentyl, 1-fluorocyclohexyl, 2-fluorocyclopropyl, 2-fluorocyclobutyl, 2-fluorocyclopentyl, 2-fluorocyclohexyl, 3-fluorocyclobutyl, 3-fluorocyclopentyl, 3-fluorocyclohexyl, 4-fluorocyclohexyl, 2,2-difluorocyclopropyl, 2,2-difluorocyclobutyl, 2,2-difluorocyclopentyl, 2,2-difluorocyclohexyl, 3,3-difluorocyclobutyl, 3,3-difluorocyclopentyl, 3,3-difluorocyclohexyl, 4,4-difluorocyclohexyl, 3,3,4,4-tetrafluorocyclopentyl, 3,3,4,4-tetrafluorocyclohexyl, 2,3-difluorocyclobutyl, 2,3-difluorocyclopentyl, 3,4-difluorocyclopentyl, 2,3-difluorocyclohexyl, 3,4-difluorocyclohexyl, 2,2,3,3-tetrafluorocyclobutyl and 2,2,3,3-tetrafluorocyclopentyl groups.

Examples of "$C_5$–$C_{15}$ saturated or unsaturated aliphatic hydrocarbon groups whose any 1 to 6 hydrogen atoms may be substituted with fluorine atoms" include $C_5$–$C_{15}$ straight chain or branched alkyl, alkenyl, alkynyl, cycloalkylidene-alkyl; cycloalkylalkyl, cycloalkylalkenyl or cycloalkylalkynyl in which optionally hydrogen atom(s) on the cycloalkyl ring may be substituted with lower alkyl; and cycloalkenylalkyl or cycloalkenylalkenyl in which optionally hydrogen atom(s) on the cycloalkenyl ring may be substituted with lower alkyl; and those whose any 1 to 6 hydrogen atom(s) are substituted with fluorine atom(s).

Specific examples of such aliphatic hydrocarbon groups include:

unsubstituted or fluorine-substituted alkyl groups such as 2-methylbutyl, 3-methylbutyl, pentyl, neopentyl, 2-methylpentyl, 3-methylpentyl, 4-methylpentyl, hexyl, 2-methylhexyl, 3-methylhexyl, 4-methylhexyl, 5-methylhexyl, 2,4-dimethylpentyl, 2-ethylhexyl, 4,5-dimethylhexyl, 4,4-dimethylpentyl, heptyl, 4-methylheptyl, octyl, nonyl, decyl, undecyl, dodecyl, tridecyl, tetradecyl, pentadecyl, 3-fluoromethylbutyl, 1-fluoropentyl, 4-fluoropentyl, 5-fluoropentyl, 1,1-difluoropentyl, 4,4-difluoropentyl, 5,5,5-trifluoropentyl, 1,1,4,4-tetrafluoropentyl, 1,1,5,5,5-pentafluoropentyl, 1-fluorohexyl, 5-fluorohexyl, 6-fluorohexyl, 1,1-difluorohexyl, 5,5-difluorohexyl, 6,6,6-trifluorohexyl, 1,1,5,5-tetrafluorohexyl, 1,1,6,6,6-pentafluorohexyl, 1-fluoro-4-methylpentyl, 2-fluoro-4-methylpentyl, 3-fluoro-4-methylpentyl, 4-fluoro-4-methylpentyl, 4-fluoromethylpentyl, 1,1-difluoro-4-methylpentyl, 4-trifluoromethylpentyl, 5,5,5-trifluoro-4-trifluoromethylpentyl, 1,1-difluoro-4-trifluoromethylpentyl, 1,1,5-trifluoro-4-methylpentyl, 1-fluoro-4-methylhexyl, 4-fluoro-4-methylhexyl, 5-fluoro-4-methylhexyl, 6-fluoro-4-methylhexyl, 1,1-difluoro-4-methylhexyl, 5,5-difluoro-4-methylhexyl, 4-trifluoromethylhexyl, 6,6,6-trifluoro-4-methylhexyl, 6,6,6-trifluoro-4-trifluoromethylhexyl, 1,1-difluoro-4-trifluormethylhexyl and 1,1-difluoro-6,6,6-trifluoro-4-methylhexyl;

unsubstituted or fluorine-substituted alkenyl groups such as 3-methyl-2-butenyl, 2-pentenyl, 3-pentenyl, 4-pentenyl, 3-methyl-2-pentenyl, 3-methyl-3-pentenyl, 4-methyl-2-pentenyl, 4-methyl-3-pentenyl, 4-methyl-4-pentenyl, 2-hexenyl, 3-hexenyl, 4-hexenyl, 4-methyl-2-hexenyl, 4-methyl-3-hexenyl, 4-methyl-4-hexenyl, 5-methyl-2-hexenyl, 5-methyl-3-hexenyl, 5-methyl-4-hexenyl, 5-methyl-2-heptenyl, 5-methyl-3-heptenyl, 5-methyl-4-heptenyl, 5-methyl-5-heptenyl, 3,4-dimethyl-2-pentenyl, 3,4-dimethyl-3-pentenyl, 4,5-dimethyl-2-hexenyl, 4,5-dimethyl-3-hexenyl, 4,5-dimethyl-4-hexenyl, octenyl, nonenyl, decenyl, undecenyl, dodecenyl, tridecenyl, tetradecenyl, pentadecenyl, 1-fluoro-4-methyl-3-pentenyl, 2-fluoro-4-methyl-3-pentenyl, (E)-4-fluoromethyl-3-pentenyl, (Z)-4-fluoromethyl-3-pentenyl, 1,1-difluoro-4-methyl-3-pentenyl, 2,2-difluoro-4-methyl-3-pentenyl, (E)-4-trifluoromethyl-3-pentenyl, (Z)-4-trifluoromethyl-3-pentenyl, (E)-1,1-difluoro-4-trifluoromethyl-3-pentenyl, (Z)-1,1-difluoro-4-trifluoromethyl-3-pentenyl, 5,5,5-trifluoro-4-trifluoromethyl-3-pentenyl, 1-fluoro-4-methyl-2-pentenyl, 4-fluoro-4-methyl-2-pentenyl, 4-fluoromethyl-2-pentenyl, 1,1-difuoro-4-methyl-2-pentenyl, 4-trifluoromethyl-2-pentenyl, 4-fluoro-1,1-difluoro-4-methyl-2-pentenyl, 1,1-difluoro-4-trifluoromethyl-2-pentenyl, 1-fluoro-4-methyl-4-pentenyl, 2-fluoro-4-methyl-4-pentenyl, 3-fluoro-4-methyl-4-pentenyl, 4-fluoromethyl-4-pentenyl, 1,1-difluoro-4-methyl-4-pentenyl, 2,2-difluoro-4-methyl-4-pentenyl, 3,3-difluoro-4-methyl-4-pentenyl, 4-trifluoromethyl-4-pentenyl, 1,1-difluoro-4-trifluoromethyl-4-pentenyl, 1,1,3,3-tetrafluoro-4-methyl-4-pentenyl, 1-fluoro-4-methyl-3-hexenyl, 2-fluoro-4-methyl-3-hexenyl, 4-fluoromethyl-3-hexenyl, 6-fluoro-4-methyl-3-hexenyl, 4-trifluoromethyl-3-hexenyl, 1,1-difluoro-4-methyl-3-hexenyl, 2,2-difluoro-4-methyl-3-hexenyl, 4-trifluoromethyl-3-hexenyl, 5,5-difluoromethyl-3-hexenyl, 6,6,6-trifluoro-4-methyl-3-hexenyl, 1,1-difluoro-4-trifluoromethyl-3-hexenyl, 1,1,-difluoro-6,6,6-trifluoromethyl-3-hexenyl and 6,6,6-trifluoro-4-trifluoromethyl-3-hexenyl;

2-pentynyl, 3-pentynyl, 4-pentynyl, 4-methyl-2-pentynyl, octynyl, nonynyl, decynyl, undecynyl, dodecynyl, tridecynyl, tetradecynyl and pentadecynyl, and those alkynyl groups in which optionally any 1 to 6 hydrogen atoms are substituted with fluorine atom(s);

unsubstituted and fluorine-substituted cycloalkylalkyl groups in which any of hydrogen atom(s) on the cycloalkyl ring may be substituted with lower alkyl, such as cyclopropylethyl, cyclopropylpropyl, cyclopropylbutyl, cyclopropylpentyl, cyclopropylhexyl, cyclopropylheptyl, cyclobutylmethyl, cyclobutylethyl, cyclobutylpropyl, cyclobutylbutyl, cyclobutylpentyl, cyclopentylmethyl, cyclopentylethyl, cyclopentylpropyl, cyclopentylbutyl, cyclohexylmethyl, cyclohexylethyl, cyclohexylpropyl, cyclohexylbutyl, cycloheptylmethyl, cycloheptylethyl, cycloheptylpropyl, cycloheptylbutyl, cyclooctylmethyl, cyclooctylethyl, cyclooctylpropyl, cyclooctylbutyl, 1-methylcyclopentylmethyl, 2-methylcyclopentylmethyl, 3-methylcyclopentylmethyl, 1-ethylcyclopentylmethyl, 2-ethylcyclopentylmethyl, 3-ethylcyclopentylmethyl, 2-cyclopentylethyl, 2-(1-methylcyclopentyl)ethyl, 2-(2-methylcyclopentyl)ethyl, 2-(3-methylcyclopentyl)ethyl, 2-(1-ethylcyclopentyl)ethyl, 2-(2-ethylcyclopentyl)ethyl, 2-(3-ethylcyclopentyl)ethyl, 1-methylcyclohexylmethyl, 2-methylcyclohexylmethyl, 3-methyloyclohexylmethyl, 4-methylcyclohexylmethyl, 1-ethylcyclohexylmethyl, 2-ethylcyclohexylmethyl, 3-ethylcyclohexylmethyl, 4-ethylcyclohexylmethyl, cyclohexylethyl, 2-(1-methylcyclohexyl)ethyl, 2-(2-methylcyclohexyl)ethyl, 2-(3-methylcyclohexyl)ethyl, 2-(4-methylcyclohexyl)ethyl, 2-(1-ethylcyclohexyl)ethyl, 2-(2-ethylcyclohexyl)ethyl, 2-(3-ethylcyclohexyl)ethyl, 2-(4-ethylcyclohexyl)ethyl, 1-methylcycloheptylmethyl, 2-methylcycloheptylmethyl, 3-methylcycloheptylmethyl, 4-methylcycloheptylmethyl, 1-ethylcycloheptylmethyl, 2-ethylcycloheptylmethyl, 3-ethylcycloheptylmethyl, 4-ethylcycloheptylmethyl, 2-cycloheptylethyl, 2-(1-methylcycloheptyl)ethyl, 2-(2-methylcycloheptyl)ethyl, 2-(3-methylcycloheptyl)ethyl, 2-(4-methylcycloheptyl)ethyl, 2-(1-ethylcycloheptyl)ethyl, 2-(2-ethylcycloheptyl)ethyl, 2-(3-ethylcycloheptyl)ethyl, 2-(4-ethylcycloheptyl)ethyl, 1-methylcyclooctylmethyl, 2-methylcyclooctylmethyl, 3-methylcyclooctylmethyl, 4-methylcyclooctylmethyl, 5-methylcyclooctylmethyl, 1-ethylcyclooctylmethyl, 2-ethylcyclooctylmethyl, 3-ethylcyclooctylmethyl, 4-ethylcyclooctylmethyl, 5-ethylcyclooctylmethyl, 2-(1-methylcyclooctyl)ethyl, 2-(2-methylcyclooctyl)ethyl, 2-(3-methylcyclooctyl)ethyl, 2-(4-methylcyclooctyl)ethyl, 2-(5-methylcyclooctyl)ethyl, 2-(1-ethylcyclooctyl)ethyl, 2-(2-ethylcyclooctyl)ethyl, 2-(3-ethylcyclooctyl)ethyl, 2-(4-ethylcyclooctyl)ethyl and 2-(5-ethylcyclooctyl)ethyl, 1-fluoro-1-cyclohexylmethyl, 2-fluorocyclohexylmethyl, 3-fluorocyclohexylmethyl, 4-fluorocyclohexylmethyl, 1,1-difluoro-1-cyclohexylmethyl, 2,2-difluorocyclohexylmethyl, 3,3-difluorocyclohexylmethyl, 4,4-difluorocyclohexylmethyl, 1-fluoro-1-cycloheptylmethyl, 2-fluorocycloheptylmethyl, 3-fluorocycloheptylmethyl, 4-fluorocycloheptylmethyl, 1,1-difluoro-1-cycloheptylmethyl, 2,2-difluorocycloheptylmethyl, 3,3-difluorocycloheptylmethyl, 4,4-difluorocycloheptylmethyl, 1-fluoro-1-(3-methylcyclohexyl)methyl, 2-fluoro-3-methylcyclohexylmethyl, 3-fluoro-3-methylcyclohexylmethyl, 4-fluoro-3-methylcyclohexylmethyl, 1,1-difluoro-1-(3-methylcyclohexyl)methyl, 2,2-difluoro-3-methylcyclohexylmethyl, 3-trifluoromethylcyclohexylmethyl, 4,4-difluoro-3-methylcyclohexylmethyl, 1-fluoro-2-cyclopentylethyl, 2-(2-fluorocyclopentyl)ethyl, 2-(3-fluorocyclopentyl)ethyl, 1,1-difluoro-2-cyclopentylethyl, 2-(2,2-difluorocyclopentyl)ethyl, 2-(3,3-difluorocyclopentyl)ethyl, 1,1-difluoro-2-(2,2-difluorocyclopentyl)ethyl and 1,1-difluoro-2-(3,3-difluorocyclopentyl)ethyl;

cycloalkylidenealkyl groups such as cyclopropylideneethyl, cyclopropylidenepropyl, cyclopropylidenebutyl, cyclopropylidenepentyl, cyclobutylideneethyl, cyclobutylidenepropyl, cyclobutylidenebutyl, cyclobutylidenepentyl, cyclopentylideneethyl, cyclopentylidenepropyl, cyclopentylidenebutyl, cyclopentylidenepentyl, cyclohexylideneethyl, cyclohexylidenepropyl, cyclohexylidenebutyl, cyclohexylidenepentyl, cycloheptylideneethyl, cycloheptylidenepropyl, cycloheptylidenebutyl, cycloheptylidenepentyl, cyclooctylideneethyl, cyclooctylidenepropyl, cyclooctylidenebutyl and cyclooctylidenepentyl, and those cycloalkylidene alkyl groups in which optionally any 1 to 6 hydrogen atoms are substituted with fluorine atom(s);

cycloalkylalkenyl groups such as cyclopropylpropenyl, cyclopropylbutenyl, cyclopropylpentenyl, cyclopropylhexenyl, cyclopropylheptenyl, cyclobutylpropenyl, cyclobutylbutenyl, cyclobutylpentenyl, cyclopentylpropenyl, cyclopentylbutenyl, cyclopentylpentenyl, cyclohexylpropenyl, cyclohexylbutenyl, cyclohexylpentenyl, cycloheptylpropenyl and cyclooctylpropenyl, and those cycloalkylalkenyl groups in which optionally any 1 to 6 hydrogen atoms are substituted with fluorine atom(s);

cycloalkylalkynyl groups such as cyclopropylpropynyl, cyclopropylbutynyl, cyclopropylpentynyl, cyclopropylhexynyl, cyclopropylheptynyl, cyclobutylpropynyl, cyclobutylbutynyl, cyclobutylpentynyl, cyclopentylpropynyl, cyclopentylbutynyl, cyclopentylpentynyl, cyclohexylpropynyl, cyclohexylbutynyl and cyclohexylpentynyl, and those cycloalkylalkynyl groups in which optionally any 1 to 6 hydrogen atoms are substituted with fluorine atom(s);

cycloalkenylalkyl groups in which any optional hydrogen atom(s) on the cycloalkenyl ring may be replaced by a lower alkyl group(s), such as cyclopropenylethyl, cyclopropenylpropyl, cyclopropenylbutyl, cyclopropenylpentyl, cyclopropenylhexyl, cyclopropenylheptyl, cyclobutenylmethyl, cyclobutenylethyl, cyclobutenylpropyl, cyclopentenylmethyl, cyclohexenylmethyl, cyclohexenylethyl, cycloheptenylmethyl, cycloheptenylethyl, cyclooctenylmethyl, cyclooctenylethyl, (1-methyl-2-cyclopentenyl)methyl, (1-methyl-3-cyclopentenyl)methyl, (2-methyl-1-cyclopentenyl)methyl, (2-methyl-2-cyclopentenyl)methyl, (2-methyl-3-cyclopentenyl)methyl, (5-methyl-2-cyclopentenyl)methyl, (5-methyl-1-cyclopentenyl)methyl, (3-methyl-1-cyclopentenyl)methyl, (3-methyl-2-cyclopentenyl)methyl, (3-methyl-3-cyclopentenyl)methyl, (4-methyl-2-cyclopentenyl)methyl, (4-methyl-1-cyclopentenyl)methyl, (1-methyl-2-cyclohexenyl)methyl, (1-methyl-3-cyclohexenyl)methyl, (2-methyl-1-cyclohexenyl)methyl, (2-methyl-2-cyclohexenyl)methyl, (2-methyl-3-cyclohexenyl)methyl, (6-methyl-3-cyclohexenyl)methyl, (6-methyl-2-cyclohexenyl)methyl, (6-methyl-1-cyclohexenyl)methyl, (3-methyl-1-cyclohexenyl)methyl, (3-methyl-2-cyclohexenyl)methyl, (3-methyl-3-cyclohexenyl)methyl, (5-methyl-3-cyclohexenyl)methyl, (5-methyl-2-cyclohexenyl)methyl, (5-methyl-1-cyclohexenyl)methyl, (4-methyl-1-cyclohexenyl)methyl, (4-methyl-2-cyclohexenyl)methyl, (4-methyl-3-cyclohexenyl)methyl, (1-methyl-2-cycloheptenyl)methyl, (1-methyl-3-cycloheptenyl)methyl, (1-methyl-4-cycloheptenyl)methyl, (2-methyl-1-cycloheptenyl)methyl, (2-methyl-2-cycloheptenyl)methyl, (2-methyl-3-cycloheptenyl)methyl, (2-methyl-4-cycloheptenyl)methyl, (7-methyl-3-cycloheptenyl)methyl, (7-methyl-2-cycloheptenyl)methyl, (7-methyl-1-cycloheptenyl)methyl, (3-methyl-1-cycloheptenyl)methyl, (3-methyl-2-cycloheptenyl)methyl, (3-methyl-3-cycloheptenyl)methyl, (3-methyl-4-cycloheptenyl)methyl, (6-methyl-3-cycloheptenyl)methyl, (6-methyl-2-cycloheptenyl)methyl, (6-methyl-1-cycloheptenyl)methyl, (4-methyl-1-cycloheptenyl)methyl, (4-methyl-2-cycloheptenyl)methyl, (4-methyl-3-cycloheptenyl)methyl, (4-methyl-4-cycloheptenyl)methyl, (5-methyl-3-cycloheptenyl)methyl, (5-methyl-2-cycloheptenyl)methyl, (5-methyl-1-cycloheptenyl)methyl, (1-methyl-2-cyclooctenyl)methyl, (1-methyl-3-cyclooctenyl)methyl, (1-methyl-4-cyclooctenyl)methyl, (2-methyl-1-cyclooctenyl)methyl, (2-methyl-2-cyclooctenyl)methyl, (2-methyl-3-cyclooctenyl)methyl, (2-methyl-4-cyclooctenyl)methyl, (8-methyl-4-cyclooctenyl)methyl, (8-methyl-3-cyclooctenyl)methyl, (8-methyl-2-cyclooctenyl)methyl, (8-methyl-1-cyclooctenyl)methyl, (3-methyl-1-cyclooctenyl)methyl, (3-methyl-2-cyclooctenyl)methyl, (3-methyl-3-cyclooctenyl)methyl, (3-methyl-4-cyclooctenyl)methyl, (7-methyl-4-cyclooctenyl)methyl, (7-methyl-3-cyclooctenyl)methyl, (7-methyl-2-cyclooctenyl)methyl, (7-methyl-1-cyclooctenyl)methyl, (4-methyl-1-cyclooctenyl)methyl, (4-methyl-2-cyclooctenyl)methyl, (4-methyl-3-cyclooctenyl)methyl, (4-methyl-4-cyclooctenyl)methyl, (6-methyl-4- cyclooctenyl)methyl, (6-methyl-2-cyclooctenyl)methyl, (6-methyl-1-cyclooctenyl)methyl, (5-methyl-1-cyclooctenyl)methyl, (5-methyl-2-cyclooctenyl)methyl, (5-methyl-3-cyclooctenyl)methyl and (5-methyl-4-cyclooctenyl)methyl, and those cycloalkenylalkyl groups in which optionally any 1 to 6 hydrogen atoms are substituted with fluorine atom(s); and cycloalkenylalkenyl groups in which any of hydrogen atoms on the cycloalkenyl ring may be substituted with lower alkyl such as cyclopropenylpropenyl, cyclopropenylbutenyl, cyclobutenylbutenyl, cyclopentenylpropenyl, cyclopentenylbutenyl, cyclopropenylpentenyl, cyclopropenylhexenyl, cyclopropenylheptenyl, cyclobutenylpropenyl, cyclohexenylpropenyl and cyclohexenylbutenyl, and those cycloalkenylalkenyl groups in which optionally any 1 to 6 hydrogen atoms are substituted with fluorine atom(s).

"Aralkyl (optionally any 1 to 3 hydrogen atoms on the ring in the aralkyl group may be substituted with lower alkyl, trifluoromethyl, cyano, hydroxyl, nitro, lower alkoxycarbonyl, halogen, lower alkoxy, amino or lower alkylamino)" signifies unsubstituted or substituted $C_7$–$C_{12}$ aralkyl groups. As their examples, unsubstituted benzyl, phenethyl, phenylpropyl and naphthylmethyl, and those substituted with above-listed substituents may be named.

"Arylalkenyl (optionally any 1–3 hydrogen atoms on the ring in the arylalkenyl group may be substituted with lower alkyl, trifluoromethyl, cyano, hydroxyl, nitro, lower alkoxycarbonyl, halogen, lower alkoxy, amino or lower alkylamino)" signifies unsubstituted or substituted $C_8$–$C_{12}$ arylalkenyl groups, examples of which include unsubstituted phenylpropenyl and naphthylpropenyl, and those substituted with above-listed substituents.

Examples of "heteroarylalkyl having 1 to 2 hetero atoms selected from a group consisting of nitrogen, oxygen and sulfur (optionally any 1–3 hydrogen atoms on the ring in the heteroarylalkyl group may be substituted with lower alkyl, trifluoromethyl, cyano, hydroxyl, nitro, lower alkoxycarbonyl, halogen, lower alkoxy, amino or lower alkylamino)" include unsubstituted 2-pyridylmethyl, 3-pyridylmethyl, 4-pyridylmethyl, 2-thiazolylmethyl, 2-thienylmethyl, 3-thienylmethyl, 1-imidazolylmethyl, 2-imidazolylmethyl, 3-pyrazolylmethyl, 4-pyrazolylmethyl, 2-furylmethyl, 3-furylmethyl, 2-pyrrolylmethyl, 3-pyrrolylmethyl, 2-pyrimidinylmethyl 4-pyrimidinylmethyl, 5-pyrimidinylmethyl, pyrazinylmethyl, 3-pyridazinylmethyl, 4-pyridazinylmethyl, 3-quinolylmethyl, 4-quinolylmethyl, 5-quinolylmethyl, 6-quinolylmethyl, 7-quinolylmethyl, 8-quinolylmethyl, 1-isoquinolylmethyl, 3-isoquinolylmethyl, 4-isoquinolylmethyl, 5-isoquinolylmethyl, 6-isoquinolylmethyl, 7-isoquinolylmethyl, 8-isoquinolylmethyl, 2-benzothienylmethyl, 3-benzothienylmethyl, 4-benzothienylmethyl, 5-benzothienylmethyl, 6-benzothienylmethyl, 7-benzothienylmethyl, 2-indolylmethyl, 3-indolylmethyl, 4-indolylmethyl, 5-indolylmethyl, 6-indolylmethyl, 7-indolylmethyl, 2-benzimidazolylmethyl, 4-benzimidazolylmethyl, 5-benzimidazolylmethyl, 2-benzothiazolylmethyl, 4-benzothiazolylmethyl, 5-benzothiazolylmethyl, 6-benzothiazolylmethyl, 7-benzothiazolylmethyl, 2-benzoxazolylmethyl, 4-benzoxazolylmethyl, 5-benzoxazolylmethyl, 6-benzoxazolylmethyl, 7-benzoxazolylmethyl, 2-benzofuranylmethyl, 3-benzofuranylmethyl, 4-benzofuranylmethyl, 5-benzofuranylmethyl, 6-benzofuranylmethyl, 7-benzofuranylmethyl, 2-pyridylethyl, 2-pyridylpropyl, 3-pyridylethyl, 4-pyridylethyl, 2-thiazolylethyl, 2-thienylethyl, 3-thienylethyl, 1-imidazolylethyl, 2-imidazolylethyl, 3-pyrazolylethyl, 4-pyrazolylethyl, 2-furylethyl, 3-furylethyl, 2-pyrrolylethyl, 3-pyrrolylethyl, 2-pyrimidinylethyl, 4-pyrimidinylethyl, 5-pyrimidinylethyl, pyrazinylethyl, 3-pyridazinylethyl, 4-pyridazinylethyl, 2-quinizylethyl, 2-benzothienylethyl, 3-benzothienylethyl, 4-benzothienylethyl, 5-benzothienylethyl, 6-benzothienylethyl, 7-benzothienylethyl, 2-indolylethyl, 3-indolylethyl, 4-indolylethyl, 5-indolylethyl, 6-indolylethyl, 7-indolylethyl, 2-benzimidazolylethyl, 4-benzimidazolylethyl, 5-benzimidazolylethyl, 2-benzothiazolylethyl, 4-benzothiazolylethyl, 5-benzothiazolylethyl, 6-benzothiazolylethyl, 7-benzothiazolylethyl, 2-benzoxazolylethyl, 4-benzoxazolylethyl, 5-benzoxazolylethyl, 6-benzoxazolylethyl, 7-benzoxazolylethyl, 2-benzofuranylethyl, 3-benzofuranylethyl, 4-benzofuranylethyl, 5-benzofuranylethyl, 6-benzofuranylethyl and 7-benzofuranylethyl, and those which are substituted with above-listed substituents.

As examples of "heteroarylalkenyl having 1–2 hetero atoms selected from the group consisting of nitrogen, oxygen and sulfur (any 1 to 3 hydrogen atoms on the ring of said heteroarylalkenyl group may be substituted with lower alkyl, trifluoromethyl, cyano, hydroxyl, nitro, lower alkoxycarbonyl, halogen, lower alkoxy, amino or lower alkylamino)", unsubstituted 2-pyridylpropenyl, 3-pyridylpropenyl, 4-pyridylpropenyl, 2-thiazolyipropenyl, 2-thienylpropenyl, 3-thienylpropenyl, 1-imidazolylbutenyl, 2-imidazolylpropenyl, 3-pyrazolylpropenyl, 4-pyrazolyipropenyl, 2-furylpropenyl, 3-furylpropenyl, 2-pyrrolylpropenyl, 3-pyrrolylpropenyl, 2-pyrimidinylpropenyl, 4-pyrimidinylpropenyl, 5-pyrimidinylpropenyl, pyrazinylpropenyl, 3-pyridazinylpropenyl, 4-pyridazinylpropenyl, 2-quinidylpropenyl, 2-benzothienylpropenyl and 2-indolylpropenyl, and those substituted with above-named substituents may be named.

"Halogen" include fluorine, chlorine, bromine and iodine.

"Lower alkyl" signifies $C_1$–$C_6$ straight chain or branched alkyl groups, for example, methyl, ethyl, propyl, isopropyl, butyl, isobutyl, sec-butyl, t-butyl, pentyl, isopentyl, hexyl and isohexyl groups.

"Lower alkoxy" signifies $C_1$–$C_6$ straight chain or branched alkoxy groups, for example, methoxy, ethoxy, propoxy, isopropoxy, butoxy, sec-butoxy, isobutoxy, t-butoxy, pentyloxy, isopentyloxy, hexyloxy and isohexyloxy groups.

"Lower alkoxycarbonyl" signifies $C_1$–$C_7$ straight chain or branched alkoxycarbonyl groups, for example, methoxycarbonyl, ethoxycarbonyl, propoxycarbonyl, isopropoxycarbonyl, butoxycarbonyl, sec-butoxycarbonyl, isobutoxycarbonyl, t-butoxycarbonyl, pentyloxycarbonyl, isopentyloxycarbonyl, hexyloxycarbonyl and isohexyloxycarbonyl groups.

"Aralkyloxycarbonyl" signifies $C_7$–$C_{10}$ aralkyloxycarbonyl groups, for example, benzyloxycarbonyl and phenethyloxycarbonyl groups.

"Lower alkylamino" signifies $C_1$–$C_6$ straight chain or branched alkylamino groups, for example, methylamino, ethylamino, propylamino, isopropylamino, butylamino, sec-butylamino, t-butylamino, pentylamino, isopentylamino, hexylamino, isohexylamino, dimethylamino, diethylamino and dipropylamino groups.

"Protected hydroxyl groups" signify hydroxyl groups which are protected with acyl such as acetyl, alkylsilyl such as trimethylsilyl and t-butyldimethylsilyl, aralkyl such as benzyl and trityl, ether group such as methoxymethyl, and in the form of alkylideneketal such as isopropylideneketal.

"Protected oxo groups" signify oxo groups which are protected in the form of acetal or ketal such as ethylene ketal, trimethylene ketal and dimethyl ketal.

"Protected amino or lower alkylamino groups" signify amino or lower alkylamino groups which are protected with, for example, aralkyl groups such as benzyl, p-methoxybenzyl, p-nitrobenzyl, benzhydryl and trityl; lower alkanoyl groups such as formyl, acetyl and propionyl; arylalkanoyl groups such as phenylacetyl and phenoxyacetyl; lower alkoxycarbonyl groups such as methoxycarbonyl, ethoxycarbonyl, isobutoxycarbonyl and t-butoxycarbonyl; alkenyloxycarbonyl groups such as 2-propenyloxycarbonyl; aralkyloxycarbonyl groups such as benzyloxycarbonyl and p-nitrobenzyloxycarbonyl, and lower alkylsilyl groups such as trimethylsilyl and t-butyldimethylsilyl. In particular, amino or lower alkylamino groups which are protected with t-butoxycarbonyl and benzyloxycarbonyl groups are preferred.

Also "deprotection" signifies removal of protective groups by the means conventionally used in the field of organic chemistry, such as hydrolysis, hydrogenolysis and the like.

Referring to the general formula [I], (1) Ar represents an aryl group or a heteroaryl group having 1 to 2 hetero atoms selected from a group consisting of nitrogen, oxygen and sulfur (any 1 to 3 hydrogen atoms on the ring of said aryl or heteroaryl group may be substituted with lower alkyl, trifluoromethyl, cyano, hydroxyl, nitro, lower alkoxycarbonyl, halogen, lower alkoxy, amino or lower alkylamino). In particular, unsubstituted phenyl or substituted phenyl having above-named substituents are preferred.

(2) $R^1$ is a $C_3$–$C_6$ cycloalkyl which may have 1 to 4 fluorine atoms on the ring; cyclobutyl, cyclopentyl, cyclohexyl, 2-fluorocyclobutyl, 3-fluorocyclobutyl, 2,2-difluorocyclobutyl, 3,3-difluorocyclobutyl, 2-fluorocyclopentyl, 3-fluorocyclopentyl, 2,2-difluorocyclopentyl, 3,3-difluorocyclopentyl, 2,2,3,3-tetrafluorocyclopentyl, 3,3,4,4-tetrafluorocyclopentyl, 2-fluorocyclohexyl, 3-fluorocyclohexyl, 4-fluorocyclohexyl, 2,2-difluorocyclohexyl, 3,3-difluorocyclohexyl and 4,4-difluorocyclohexyl being preferred.

Of these, particularly 2-fluorocyclobutyl, 3-fluorocyclobutyl, 2,2-difluorocyclobutyl, 3,3-difluorocyclobutyl, 2-fluorocyclopentyl, 3-fluorocyclopentyl, 2,2-difluorocyclopentyl, 3,3-difluorocyclopentyl, 2,2,3,3-tetrafluorocyclopentyl, 3,3,4,4-tetrafluorocyclopentyl, 2-fluorocyclohexyl, 3-fluorocyclohexyl, 4-fluorocyclohexyl, 2,2-difluorocyclohexyl, 3,3-difluorocyclohexyl and 4,4-difluorocyclohexyl are preferred. 3,3-Difluorocyclopentyl is the best preferred.

(3) X represents O or NH, NH being the preferred.

(4) $R^2$ represents $C_5$–$C_{15}$ saturated or unsaturated aliphatic hydrocarbon groups whose any 1 to 6 hydrogen atoms may be substituted with fluorine atom(s), aralkyl, arylalkenyl, heteroarylalkyl or heteroarylalkenyl group having 1 to 2 hetero atoms selected from a group consisting of nitrogen, oxygen and sulfur (optionally any 1 to 3 hydrogen atoms on the ring in said aralkyl, arylalkenyl, heteroarylalkyl or heteroarylalkenyl group may be substituted with lower alkyl, trifluoromethyl, cyano, hydroxyl, nitro, lower alkoxycarbonyl, halogen, lower alkoxy, amino or lower alkylamino). Of these, the groups expressed by the following formula [II], in which any 1 to 6 hydrogen atoms may be substituted with fluorine atom(s),

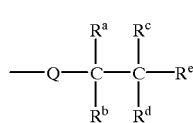

[II]

[in which

Q represents methylene, ethylene, trimethylene or tetramethylene;

$R^a$ and $R^c$ each represents a hydrogen atom or are combined to form a single bond; and $R^b$, $R^d$ and $R^e$ may be the same or different and each represents a hydrogen atom, a lower alkyl group, $C_3$–$C_8$ cycloalkyl or cycloalkenyl, or $R^b$ and $R^d$, or $R^d$ and $R^e$ together form each a $C_3$–$C_8$ cycloalkyl or cycloalkenyl], benzyl, phenethyl, phenylpropyl, phenylpropenyl, 2-pyridylmethyl, 2-pyridylethyl, 2-pyridylpropyl, 3-pyridylmethyl, 4-pyridylmethyl, 2-thiazolylmethyl, 2-thienylmethyl, 3-thienylmethyl, 1-imidazolylmethyl, 2-imidazolylmethyl, 4-imidazolylmethyl, 2-furylmethyl, 3-furylmethyl, 2-pyrrolylmethyl, 3-pyrrolylmethyl (any 1 to 3 hydrogen atoms on the ring of said benzyl, phenethyl, phenylpropyl, phenylpropenyl or heteroarylalkyl group may be substituted with lower alkyl, trifluoromethyl, cyano, hydroxyl, nitro, lower alkoxycarbonyl, halogen, lower alkoxy, amino or lower alkylamino) are preferred.

In particular, 2-thienylmethyl, 3-thienylmethyl, 2-furylmethyl, 3-furylmethyl, 2-pyridylmethyl or benzyl (any 1–3 hydrogen atoms on the ring in the thienylmethyl, furylmethyl, pyridylmethyl or benzyl group may be substituted with lower alkyl, trifluoromethyl, cyano, hydroxyl, nitro, lower alkoxycarbonyl, halogen, amino, lower alkylamino or lower alkoxy) are preferred, inter alia, 6-aminopyridin-2-ylmethyl group is preferred.

According to the manner of substitution, the compounds of the present invention may exist in the form of stereoisomers such as optical isomers, diastereoisomers and geometrical isomers. It is to be understood that the compounds of the present invention also include all such stereoisomers and mixtures thereof.

Moreover, the compounds of the present invention may exist in the form of pharmaceutically acceptable salts. Such salts include inorganic acid salts such as hydrochlorides, sulfates, nitrates, phosphates and perchlorates; organic carboxylic acid salts such as maleates, fumarates, succinates, tartrates, citrates and ascorbates; organic sulfonic acid salts such as methanesulfonates, isethionates, benzenesulfonates and p-toluenesulfonates; and the like.

The compounds of the above general formula [I] in accordance with the present invention can be prepared, for example, by:

(a) reacting a carboxylic acid of the general formula [III]

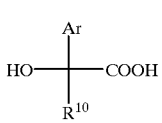

[III]

[wherein Ar represents an aryl group or a heteroaryl group having 1 to 2 hetero atoms selected from a group consisting of nitrogen, oxygen and sulfur (any 1 to 3 hydrogen atoms on the ring of said aryl or heteroaryl group may be substituted with lower alkyl, trifluoromethyl, cyano, hydroxyl, nitro, lower alkoxycarbonyl, halogen, lower alkoxy, amino or lower alkylamino); and $R^{10}$ represents a $C_3$–$C_6$ cycloalkyl in which any 1 to 4 hydrogen atoms may be substituted with fluorine atom(s) or a $C_3$–$C_6$ cycloalkyl having 1 to 2 protected or unprotected hydroxyl or oxo group(s)] or a reactive derivative thereof with a compound of the general formula [IV]

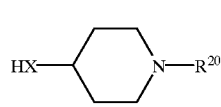

[IV]

[wherein $R^{20}$ represents a $C_5$–$C_{15}$ saturated or unsaturated aliphatic hydrocarbon group in which any 1 to 6 hydrogen atoms may be substituted with fluorine atom(s), $C_{15}$–$C_{15}$ saturated or unsaturated aliphatic hydrocarbon group having 1–2 protected or unprotected hydroxyl or oxo group(s), aralkyl, arylalkenyl, heteroarylalkyl or heteroarylalkenyl group having 1 to 2 hetero atoms selected from a group consisting of nitrogen, oxygen and sulfur (optionally any 1 to 3 hydrogen atoms on the ring in said aralkyl, arylalkenyl, heteroarylalkyl or heteroarylalkenyl group may be substituted with lower alkyl, trifluoromethyl, cyano, hydroxyl, nitro, lower alkoxycarbonyl, halogen, lower alkoxy, unprotected or protected amino, unprotected or protected lower alkylamino or aralkyloxycarbonyl group) and X stands for NH or O];
and when either $R^{10}$ or $R^{20}$ has unprotected or protected 1 to 2 hydroxyl or oxo group(s) converting said hydroxyl or oxo groups to fluorine atom(s) either as they are or after removing the protective group(s); when $R^{10}$ or $R^{20}$ has protected amino or protected lower alkylamino group(s), removing the protective group(s); and when $R^{10}$ or $R^{20}$ has lower alkoxycarbonyl or aralkyloxycarbonyl, converting the same to amino; or
(b) reacting a carboxylic acid of the above general formula [III] or a reactive derivative thereof with a compound of the general formula [V]

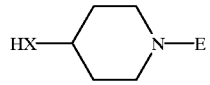

[V]

[wherein E is a protective group for the imino group, and X is as defined above]
or a salt thereof; deprotecting the resulting compound of the general formula [VI]

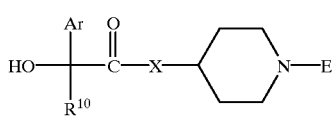

[VI]

[wherein Ar, $R^{10}$, X and E are as defined above]
thereafter reacting the same with a compound of the general formula [VII]

$R^{20}$—L  [VII]

[wherein L represents a leaving group, and $R^{20}$ is as defined above]
in the presence of a base, if necessary, and again if necessary conducting a conversion reaction of $R^{10}$ and $R^{20}$ similar to the above; or
(c) deprotecting a compound of the above general formula [VI] and subjecting it to a reductive alkylation reaction with a compound of the general formula [VIII]

$R^{21}$—CHO  [VIII]

[wherein $R^{21}$ represents a $C_4$–$C_{14}$ saturated or unsaturated aliphatic hydrocarbon group in which any 1 to 6 hydrogen atom(s) may be substituted with fluorine atom(s), $C_4$–$C_{14}$ saturated or unsaturated aliphatic hydrocarbon group having unprotected or protected 1 to 2 hydroxyl or oxo group(s), aryl, aralkyl, arylalkenyl or heteroaryl, heteroarylalkyl or heteroarylalkenyl having 1 to 2 hetero atoms selected from a group consisting of nitrogen, oxygen and sulfur (optionally any 1–3 hydrogen atoms on the ring in said aryl, aralkyl, arylalkenyl, heteroaryl, heteroarylalkyl or heteroarylalkenyl group may be substituted with lower alkyl, trifluoromethyl, cyano, hydroxyl, nitro, lower alkoxycarbonyl, halogen, lower alkoxy, unprotected or protected amino, unprotected or protected lower alkylamino or aralkyloxycarbonyl)],
and if necessary conducting the conversion reaction of $R^{10}$ and $R^{21}$ similar to the foregoing.

In the above formula [VII], "leaving groups" represented by L include, for example, halogen atoms such as chlorine, bromine and iodine; alkylsulfonyloxy groups such as methanesulfonyloxy; and arylsulfonyloxy groups such as p-toluenesulfonyloxy.

In the above formulae [V] and [VI], "protective groups for the imino group" represented by E signify similar protective groups to those for amino as above.

In the above-described process variant (a), a carboxylic acid of formula [III] is reacted with a compound of formula [IV] or a salt thereof in the presence of a suitable condensing agent. Thus, there is obtained a coupled compound of the general formula [IX]

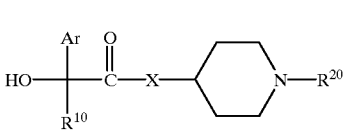

[IX]

[wherein Ar, $R^{10}$, X and $R^{20}$ are as defined above].

The carboxylic acid of formula [III] used as a starting material in the above condensation reaction can be prepared, for example, by the method as described in Referential Examples.

The condensing agent to be used in the above-described reaction may be any of those which are commonly used in the field of organic synthetic chemistry for condensation reactions of carboxyl groups with hydroxyl or amino groups, and examples thereof include N,N'-dicyclohexylcarbodiimide, 1-ethyl-3-(3-dimethylaminopropyl)carbodiimide, diphenylphosphoryl azide and dipyridyl disulfide-triphenylphosphine. Of these, 1-ethyl-3-(3-dimethylaminopropyl)carbodiimide is preferred.

Use rate of these condensing agents are subject to no critical limitation, while normally it may be within a range of 1 to 5 equivalents, preferably 1 to 2 equivalents, per mole of the compound of formula [III].

If necessary, the above-described condensation reaction may be carried out in the presence of a base. Bases which can be used for this purpose include, for example, aliphatic tertiary amines such as triethylamine and diisopropylethylamine; and aromatic amines such as pyridine, 4-dimethylaminopyridine, quinoline. 4-Dimethylaminopyridine is particularly preferred.

The condensation reaction is preferably carried out in an inert solvent. Suitable inert organic solvents include, for example, diethyl ether, tetrahydrofuran, N,N-dimethylformamide, dioxane, benzene, toluene, chlorobenzene, methylene chloride, chloroform, carbon tetrachloride, dichloroethane, trichloroethylene and mixtures of the foregoing solvents. Of these, diethyl ether, tetrahydrofuran, N,N-dimethylformamide and dioxane are preferred.

The reaction temperature may usually range from $-70°$ C. to the boiling point of the solvent used for the reaction and preferably from $-20°$ C. to $100°$ C. Under these conditions, the reaction can usually be completed in a period of time ranging from 5 minutes to 7 days and preferably from 10 minutes to 24 hours.

The proportion of the compound of formula [IV] or a salt thereof to the compound of formula [III] is not critical and may vary according to the kinds of individual compounds, the reaction conditions employed and other factors. Whereas, the compound of formula [IV] or a salt thereof may usually be used in an amount of 1 to 5 moles, preferably 1 to 2 moles, per mole of the compound of formula [III].

The coupled compound of the above formula [IX] can also be obtained by converting the carboxylic acid of formula [III] into a reactive derivative thereof and condensing it with the compound of formula [IV] or a salt thereof.

Suitable reactive derivatives of the carboxylic acid of formula [III] include, for example, compounds which are commonly used in the field of organic synthetic chemistry for activation of carboxyl group(s) in an esterification or amidation reaction, such as mixed acid anhydrides, active esters and active amides.

Mixed acid anhydrides of the carboxylic acid of formula [III] can be obtained by reacting the carboxylic acid of formula [III] with an alkyl chlorocarbonate, e.g., ethyl chlorocarbonate, an aliphatic carboxylic acid chloride, e.g., acetyl chloride, pivaloyl chloride or the like according to conventional method. Reactive esters thereof can be obtained by reacting the carboxylic acid of formula [III] with an N-hydroxy compound, e.g., N-hydroxysuccinimide, N-hydroxyphthalimide or 1-hydroxybenzotriazole; or a phenol compound, e.g., 4-nitrophenol, 2,4-dinitrophenol, 2,4,5-trichlorophenol, pentachlorophenol or the like; in the presence of a condensing agent, e.g., N,N'-dicyclohexylcarbodiimide, 1-ethyl-3-(3-dimethylaminopropyl)carbodiimide, diphenylphosphoryl azide or dipyridyl disulfide-triphenylphosphine, according to conventional method. Reactive amides thereof can be obtained by reacting the carboxylic acid of formula [III] with 1,1'-carbonyldiimidazole, 1,1'-carbonylbis(2-methylimidazole) or the like according to conventional method.

The condensation reaction of a reactive derivative of a carboxylic acid of formula [III] with a compound of formula [IV] or a salt thereof is preferably carried out in an inert solvent. Suitable inert organic solvents include, for example, diethyl ether, tetrahydrofuran, N,N-dimethylformamide, dioxane, benzene, toluene, chlorobenzene, methylene chloride, chloroform, carbon tetrachloride, dichloroethane, trichloroethylene and mixtures of the foregoing solvents. Of these, diethyl ether, chloroform, tetrahydrofuran, N,N-dimethylformamide and dioxane are preferred.

The reaction temperature may usually range from $-70°$ C. to the boiling point of the solvent used for the reaction and preferably from $-20°$ C. to $100°$ C.

The proportion of the compound of formula [IV] or a salt thereof to the reactive derivative of a carboxylic acid of formula [III] is not critical and may vary according to the kind of the reactive derivative and other factors, while the compound of formula [IV] or a salt thereof may usually be used in an amount of 1 to 5 moles, preferably 1 to 2 moles, per mole of the reactive derivative of the carboxylic acid of formula [III].

In the coupled compounds expressed by the general formula [IX], when $R^{10}$ is a $C_3$–$C_6$ cycloalkyl group having 1–2 unprotected or protected hydroxyl or oxo group(s), or $R^{20}$ is an aliphatic hydrocarbon group having 1–2 unprotected or protected hydroxyl or oxo group(s), the hydroxyl or oxo group(s) are converted to fluorine atom(s) either as they are or after removing the protective group(s).

Removal of protective groups from hydroxyl and oxo groups which are protected in the form of ketals in the compounds of formula [IX] can normally be effected in aqueous solvent, using an inorganic acid, an organic acid, a weakly acidic salt or the like. Suitable inorganic acids include, for example, hydrochloric acid and sulfuric acid; suitable organic acids include, for example, p-toluenesulfonic acid, benzenesulfonic acid, camphorsulfonic acid and acetic acid; and suitable weakly acidic salts include, for example, ammonium chloride and pyridinium p-toluenesulfonate. Preferred aqueous solvents include aqueous methanol, aqueous ethanol, aqueous tetrahydrofuran, aqueous dioxane and the like. The reaction may usually be carried out in the presence of a catalytic amount to 5 equivalents, preferably a catalytic amount to 1 equivalent, of such an acid or salt at a temperature ranging from $0°$ C. to $100°$ C. and preferably from room temperature to $80°$ C.

Conversion of the hydroxyl or oxo group(s) to fluorine atom(s) can normally be effected by causing the compound to react in an inert solvent which is not detrimental to the reaction, e.g., methylene chloride, chloroform, tetrahydrofuran, methanol, acetonitrile, dimethylsulfoxide or pyridine, or in the absence of a solvent, using one equivalent to an excessive amount, preferably 1–2 equivalents, of a fluorinating agent such as sulfurtetrafluoride, diethylaminosulfurtrifluoride, cesium fluorosulfate, tetrabutylammonium fluoride, tris(dimethylamino)sulfonium-difluorotrimethylsilicate, hydrogen fluoride or tosyl fluoride, preferably at temperatures ranging $-80°$ C.–$180°$ C. for 10 minutes to 72 hours.

When $R^{20}$ in the compounds expressed by general formula [IV] or [IX] has protected amino group(s) or protected lower alkylamino group(s), the protective group(s) are removed if necessary; when lower alkoxycarbonyl or aryloxycarbonyl group(s) are present, the functional group(s) are suitably converted to amino group(s). Removal of amino-protective groups can be effected by processes known per se, for example, any of those described in *Protective Groups in Organic Synthesis,* T. W. Greene, John Wiley & Sons Co. (1981) or methods analogous thereto, for example, solvolysis using an acid or base, chemical reduction using a metal hydride complex or the like and catalytic reduction using palladium-on-carbon, Raney-nickel or the like.

Solvolysis with an acid can normally be carried out by treating the compound with an acid such as formic acid, trifluoroacetic acid, hydrochloric acid or sulfuric acid, in an inert solvent such as methylene chloride, anisole, tetrahydrofuran, dioxane, methanol or ethanol or a mixture of such a solvent and water, or in the absence of solvent, preferably at a temperature in the range from about 0° to about 100° C., for a period of time ranging from 10 minutes to 24 hours.

Solvolysis with a base can normally be carried out by treating the compound with an alkali metal hydroxide, e.g., lithium hydroxide, sodium hydroxide or potassium hydroxide; an alkali metal carbonate, e.g., sodium carbonate or potassium carbonate, in an inert solvent which exerts no adverse effect on the reaction, e.g., methanol, ethanol, isopropanol, tetrahydrofuran or dioxane or a mixture of such a solvent and water, preferably at a temperature in the range of from about −20 to about 80° C., for a period of time ranging from 10 minutes to 24 hours.

Catalytic reduction can normally be carried out in the presence of a catalyst such as palladium-on-carbon, palladium hydroxide, Raney nickel or platinum oxide, in an inert solvent, e.g., methanol, ethanol, water or acetic acid or a mixture of such solvents, preferably under a pressure of hydrogen of about 1 to about 20 kg/cm$^2$, preferably at a temperature in the range of from about 0 to about 40° C., for a period of time ranging from 10 minutes to 24 hours.

Conversion of the lower alkoxycarbonyl or aryloxycarbonyl to amino can be conducted by either reacting the compound with hydrazine to form an acid hydrazide and thereafter converting it to the corresponding acid azide; or converting the compound to a carboxylic acid by hydrolysis, then to an acid azide, followed by rearrangement and hydrolysis.

In the process variant (b), the condensation reaction of a carboxylic acid of formula [III] or a reactive derivative thereof with a piperidine derivative of formula [V] in the first stage can be practiced in the manner similar to the condensation reaction of a carboxylic acid of formula [III] or a reactive derivative thereof with a compound of formula [IV] in the process variant (a).

The compound of the foregoing formula [VI] obtained through this condensation reaction is then removed of the protective group(s) of imino group(s).

Removal of said imino-protective groups from a compound of formula [VI] can be effected in the manner similar to above-described removal of amino-protective groups.

Thus obtained compounds of the general formula [X]

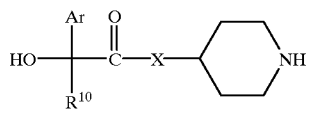

[X]

[wherein Ar, R$^{10}$ and X are as defined above] is reacted with a compound of formula [VII] in the second stage, if necessary in the presence of a base.

The reaction of the compound of formula [X] with the compound of formula [VII] is usually carried out in a suitable solvent by using the compounds in substantially equimolar amounts or using either of the compounds in slight excess (e.g., using the compound of formula [VII] in an amount of 1 to 1.3 moles per mole of the compound of formula [X]). If desired, however, either of the compounds may be used in large excess. Moreover, a suitable base and/or an additive may be used.

Suitable solvents include, for example, ethers such as diethyl ether, tetrahydrofuran and dioxane; aromatic hydrocarbons such as benzene, toluene, chlorobenzene and xylene; aprotic polar solvents such as dimethyl sulfoxide, N,N-dimethylformamide, acetonitrile and hexamethyiphosphoric triamide; and mixtures thereof.

Bases which can be used for above-described reaction include, for example, alkali metal bicarbonates such as sodium hydrogen carbonate and potassium hydrogen carbonate; alkali metal carbonates such as sodium carbonate and potassium carbonate; tertiary aliphatic amines such as trimethylamine, triethylamine, N,N-diisopropylethylamine, N-methylmorpholine, N-methylpyrrolidine, N-methylpiperidine, N,N-dimethylaniline, 1,8-diazabicyclo [5.4.0]undec-7-ene (DBU) and 1,5-diazabicyclo[4.3.0]non-5-ene (DBN); and aromatic amines such as pyridine, 4-dimethylaminopyridine, picoline, lutidine, quinoline and isoquinoline. Of these, N,N-diisopropylethylamine and potassium carbonate are preferred.

Additives which can be used for above-described reaction include, for example, alkali metal iodides such as lithium iodide, sodium iodide and potassium iodide. Of these, potassium iodide is preferred.

The reaction temperature may usually range from about 0° C. to the boiling point of the solvent, and the reaction time may usually range from 10 minutes to 48 hours. If desired, however, reaction conditions beyond these limits may be used.

If necessary, furthermore, conversion reactions of R$^{10}$ and R$^{20}$ as described as to the process variant (a) are conducted.

The reductive alkylation reaction of a compound of the above formula [X] with an aldehyde of formula [VIII] according to the process variant (c) is normally carried out in an inert solvent which exerts no adverse effect on the reaction. Suitable inert solvents include, for example, alcohols such as methanol and ethanol; ethers such as diethyl ether, tetrahydrofuran and dioxane; aromatic hydrocarbons such as benzene and toluene; and mixtures thereof. Of these, methanol, ethanol, tetrahydrofuran and toluene are preferred.

The reaction temperature may usually range from about −30° C. to about 200° C. and preferably from about 0° C. to about 100° C. The reaction time may usually range from 10 minutes to 7 days and preferably from 10 minutes to 24 hours.

The above-described reductive alkylation reaction is preferably carried out under weakly acidic conditions which facilitate formation of Schiff bases. Acids which can be used for the necessary pH control include, for example, p-toluenesulfonic acid, hydrochloric acid, acetic acid and trifluoroacetic acid.

The reductive alkylation can be effected, for example, using a metal hydride complex such as sodium borohydride, sodium cyanoborohydride, lithium aluminum hydride or sodium triacetoxyborohydride, or by catalytic reduction using a palladium-on-carbon catalyst, a Raney nickel catalyst or the like. Preferably, it is effected using a metal hydride complex such as sodium borohydride or sodium cyanoborohydride. Especially when the reductive alkylation is carried out under weakly acidic conditions which facilitate formation of Schiff bases, it is preferable to use sodium cyanoborohydride or the like which are relatively stable in the acidic pH range.

When a metal hydride complex is used as the reducing agent, the amount of reducing agent used may usually range from 1 mole to excessive moles, preferably from 1 to 10 moles, per mole of the compound of formula [X].

If necessary, then the conversion reactions of $R^{10}$ and $R^{21}$ as described as to the process variant (a) are carried out.

The compounds of formula [I] which are obtained according to the above-described process variants (a), (b) and (c) can be isolated and purified by those methods known per se, i.e. such customarily used separation means as column chromatography using silica gel, adsorbent resin or the like, liquid chromatography, thin-layer chromatography, solvent extraction or recrystallization and reprecipitation.

The compounds of the present invention and intermediates thereof exist in stereoisomeric forms such as enantiomeric isomers, diastereoisomers and geometrical isomers. It is to be understood that the compounds of the present invention also include all such stereoisomerically pure substances and mixtures thereof. When the compounds of the present invention and intermediates thereof are racemates, their optical resolution can be achieved by conventional means such as high-performance liquid chromatography using a chiral carrier or fractional crystallization of a diastereomeric salt.

The compounds of formula [I] obtained in the above-described manner may be converted into pharmaceutically acceptable salts thereof according to usual manner. Conversely, such salts may also be converted into the corresponding free amines according to usual manner.

The compounds of formula [I] in accordance with the present invention exhibit potent and selective inhibitory activity for binding to muscarinic receptors, a potent and selective antagonism to muscarinic receptors in vitro and, furthermore, potent and durable bronchodilatory action in vivo. These activities exhibited by the compounds of the present invention are demonstrated by the following tests on the inhibition of binding to muscarinic receptors and tests on antagonism against various muscarinic receptors.

Tests on inhibition of binding to muscarinic receptors

These tests were performed according to a modification of the method of Hargreaves et al. (Br. J. Pharmacol. 107: 494–501, 1992). Membranes from CHO cells expressing cloned human m1–m5 (Receptor Biology, Inc.) were incubated with 0.2 nM [$^3$H]-N-methylscopolamine and each a compound of the present invention to be tested in 0.5 ml of 50 mM Tris-HCl—10 mM $MgCl_2$—1 mM EDTA (pH 7.4) for 2 hours at 25° C. Free and membrane-bound [$^3$H]-N-methylscopolamine were separated by filtration over glass filters (UniFilter-GF/C; Packard Instruments Co., Inc.) using cell harvester (Filtermate™ 196; Packard Instruments Co., Inc.). Then the filter was washed four times with 1 ml of ice-cold Tris-HCl (pH 7.4) and dried at 50° C. After adding a scintillator (Microscinti 0; Packard Instruments Co., Inc.), the radioactivity was counted by a liquid scintillation counter (TopCount™; Packard Instruments Co., Inc.). Non-specific binding was measured in the presence of 1 μM N-methylscopolamine. According to the method of Cheng and Prussoff (Biochem. Pharmacol. 22: 3099–3108, 1973), the binding affinity (Ki value) of the test compound (i.e., a compound of the present invention) for muscarinic receptors was calculated from the concentration of the test compound which achieved 50% inhibition of binding of [$^3$H]-N-methylscopolamine ($IC_{50}$ value).

TABLE 1

Inhibitory Effects on Binding to Muscarinic $M_2$ and $M_3$ Receptors

| | Ki (nM) | | |
|---|---|---|---|
| | $M_2$ | $M_3$ | $M_2/M_3$ |
| Compound of Example 1 | 3200 | 5.5 | 590 |
| Compound of Example 10 | 17000 | 8.9 | 1900 |
| Compound of Example 11 | 460 | 3.2 | 140 |
| Compound of Example 12 | 8600 | 30 | 290 |
| Compound of Example 14 | 1400 | 10 | 140 |
| Compound of Example 15 | 1000 | 3.5 | 290 |
| Compound of Example 20 | 550 | 3.0 | 180 |
| Compound of Example 21 | 50000 | 22 | 2300 |
| Compound of Example 22 | 13000 | 19 | 680 |
| Compound of Example 26 | 24000 | 22 | 1100 |
| Compound of Example 27 | 4200 | 20 | 210 |
| Compound of Example 31 | 10000 | 19 | 520 |

As is clear from the results indicated in above Table 1, those compounds of the present invention exhibited far higher binding-inhibitory activity to $M_3$ receptor, than to $M_2$ receptor.

Tests for Antagonism to Muscarinic Receptors (in vitro)

1) Tests for antagonism to $M_2$ receptor in an isolated rat right atrium

These tests were performed according to a conventional method. A male SD strain rat (weighing 300–500 g) was killed by exsanguination, and the right atrium was isolated. This preparation was isometrically suspended in organ bath filled with 20 ml of Krebs-Henseleit solution (gassed with 95% $O_2$—5% $CO_2$ and kept at 32° C.) with an initial tension of 0.5 g. The heart rate was recorded with a heart rate counter. After the preparation was equilibrated for 30 minutes, carbachol ($10^{-9}$ to $10^{-6}$ M) was cumulatively administered in three-fold increasing doses. Thus, a decrease in heart rate was measured to obtain a dose-response curve for the control experiment. After the preparation was washed with fresh solution to restore the heart rate, a test compound was administered thereto. Ten minutes later, carbachol was cumulatively administered again. Responses to carbachol were expressed as percentages based on the heart rate before administration of carbachol as 100%. The antagonistic potency ($K_B$ value) of the test compound was determined from the degree of shift of the dose-response curve obtained by treatment with individual test compound of the present invention.

2) Tests for antagonism to the airway $M_3$ receptor in an isolated rat trachea

These tests were performed according to a conventional method. A male SD strain rat (weighing 300–500 g) was killed by exsanguination, and the trachea was isolated. Annular segments (2 mm wide) were cut out from the trachea and cut transversely at the anterior cartilage part to make open ring preparation. A preparation was suspended in a Magnus tube filled with 5 ml of Krebs-Henseleit solution (gassed with 95% $O_2$—5% $CO_2$ and kept at 32° C.) with an initial tension of 1.0 g and a resting tension of 0.6 g. The tension of the preparation was recorded isometrically. After being equilibrated for an hour, the preparation was made to contract twice by treatment with $10^{-4}$ M carbachol, and the second contraction induced by carbachol was used as the reference contraction. After the preparation was washed with fresh solution to be restored to the base line, a test compound was administered thereto (or no treatment was given). Ten minutes later, carbachol ($10^{-8}$ to $10^{-3}$ M) was cumulatively administered in three-fold increasing doses to obtain a dose-response curve. The dose-response curve was plotted by expressing responses as percentages based on the reference contraction of the preparation as 100%. The antagonistic potency ($K_B$ value) of the test compound was determined from the degree of shift of the dose-response curve obtained by treatment with the test compound.

TABLE 2

Antagonism to Muscarinic Receptors (in vitro)

$K_B$ (nM)

| | right atrium $M_2$ | Trachea $M_3$ | $M_2/M_3$ |
|---|---|---|---|
| Compound of Example 1 | 1000 | 6.3 | 160 |
| Compound of Example 11 | 610 | 0.95 | 640 |
| Compound of Example 20 | 2100 | 1.6 | 630 |

As is clear from the results indicated in above Table 2, the compounds of the present invention exhibited far more powerful antagonism to the trachea $M_3$ receptor than to the right atrium $M_2$ receptor. Therefore, the compounds of the present invention are more selective for trachea $M_3$ receptor. Tests for antagonism against muscarinic $M_3$ receptor (in vivo)

1-A) Tests for bronchodilation in rats (i.v.)

Eight- to eleven-weeks-old male rats of the Sprague-Dawley strain, weighing 380–420 g, were anesthetized with urethane (750 mg/kg. i.p.) and α-chloralose (37.5 mg/kg, i.p.). The bronchus of each rat was intubated, and the right jugular vein was cannulated for drug administration. After spontaneous respiration was fully suppressed by succinylcholine (5 mg/kg, s.c.), the airway resistance was measured under artificial ventilation by means of a Pulmonary Mechanics Model 6 (Buxco). To evoke an increase in airway resistance, acetylcholine (50 μg/kg, i.v.) was administered to the animals. The acetylcholine-induced airway resistance increase was measured 5 minutes before and 5 minutes after administration of test compound, and the ratio of the airway resistance of the latter to the former was calculated. In controls, isotonic sodium chloride solution was used in place of the test compounds and otherwise identical procedures were repeated, the calculated ratio being set to be 100%. A dose that inhibited the acetylcholine-induced increase in airway resistance in the control groups by 50% was defined to be $ED_{50}$, and the $ED_{50}$ values of the test compounds were calculated by probit analysis of their dose-response curves.

1-B) Tests for bronchodilation in rats (p.o.)

Eight- to eleven-weeks-old male rats of Sprague-Dawley strain weighing 380–420 g were orally administered with a test compound. The rats were treated in the identical manner as in the i.v. test, starting 30 minutes after the administration, and their airway resistance values were measured. The acetylcholine-(50 μg/kg, i.v.) induced airway resistance increase were measured 60 minutes after the administration of test compounds. In controls, isotonic sodium chloride solution was used in place of the test compounds and otherwise identical procedures were repeated, the ratio between the two airway resistance values whereby being set to be 100%. A dose that inhibited the acetylcholine-induced increase in airway resistance in the control groups by 50% was defined to be $ED_{50}$, and the $ED_{50}$ values of the test compounds were calculated by probit analysis of their dose-response curves.

TABLE 3

Antagonism to Muscarinic Receptor (in vivo)

| | Inhibition of Airway Contraction $ED_{50}$ (mg/kg) | |
|---|---|---|
| | iv | po |
| Compound of Example 1 | 0.033 | — |
| Compound of Example 11 | 0.032 | 0.22 |
| Compound of Example 20 | 0.040 | 0.37 |
| Compound of Example 26 | 0.37 | 0.95 |
| atoropine | 0.0043 | — |
| ipratropium | 0.0015 | — |

2) Tests for bronchodilation in dogs (p.o.)

Twelve- to twenty-four-months-old male beagle dogs (weighing 10–15 kg) were anesthetized with pentobarbital (30 mg/kg, i.v.) and intubated in their bronchus. Their airway sensitivity to inhaled methacholine were measured at least twice at two-weeks interval, and the dogs showing a reproducible methacholine reaction threshold values[1] ware selected. To those dogs whose methacholine reaction threshold value had been confirmed, the test compounds were orally administered (1 mg/kg). Four hours after the administration, the methacholine provocation test was conducted, and then the methacholine reaction threshold value[2] after administration of the test compound was obtained.

The bronchodilator activity of the test compound was determined following equation:

$$\text{shift value} = \frac{\text{methacholine reaction threshold value}^{1)} \text{ after drug administration}}{\text{methacholine reaction threshold value}^{2)} \text{ without drug administration}}$$

The methacholine provocation test was conducted using Astograph TCK-6100H Model (Chest). Methacholine chloride was used as bronchoconstritor, which was diluted with isotonic sodium chloride solution in 10-grade concentration levels starting from 40,000 μg/ml, as 20,000, 10,000, 5,000, 2,500, 1,250, 625, 312.5, 156 and 78 μg/ml. These methacholine aerosols were inhaled to the test animal each for 1 min, starting from the lowest concentration level, and respiration resistance was continuously recorded. The concentration level at which the respiration resistance reached twice the initial value was recorded as the methacholine threshold value.

TABLE 4

Bronchodilation Activity in Dogs (Oral Administration)

| | Methacholine Inhalation-inducing Test (1 mg/kg, p. o.) shift value (after 4 hrs.) |
|---|---|
| Compound of Example 11 | 21 |
| Compound of Example 20 | >69 |
| Compound of Example 26 | >64 |

As clearly demonstrated in above Table 4, the compounds of the present invention exhibited powerful bronchodilation action and long duration of the action.

As above, the compounds of formula [I] of the present invention, which are characterized by introduction of fluorine atom(s) thereinto, exhibit potent and selective antagonistic activity against muscarinic $M_3$ receptors and exhibit excellent oral activity, duration of action and pharmacokinetics. Hence, they can be administered to patients orally or parenterally as safe pharmaceutics exhibiting little side effects, in the treatment or prophylaxis of diseases such respiratory diseases as chronic obstructive pulmonary diseases, chronic bronchitis, asthma and rhinitis: digestive diseases such as irritable bowel syndrome, convulsive colitis, diverticulitis and pain accompanying contraction of smooth muscles of the digestive system: urinary disorders like urinary incontinence and frequency in neurogenic pollakiurea, neurogenic bladder, nocturnal enuresis, unstable bladder; cystospasm and chronic cystisis: and motion sickness.

In practically using the compounds of the present invention for the treatment or prophylaxis of such diseases, they may be combined with pharmaceutically acceptable adjuvants in the usual manner to prepare pharmaceutical compositions suitable for administration. For this purpose, there can be used a variety of adjuvants which are commonly used in the field of pharmaceutics. Such adjuvants include, for example, gelatin, lactose, sucrose, titanium oxide, starch, crystalline cellulose, hydroxypropylmethylcellulose, carboxymethylcellulose, corn starch, microcrystalline wax, white petrolatum, magnesium aluminate metasilicate, anhydrous calcium phosphate, citric acid, trisodium citrate, hydroxypropyl cellulose, sorbitol, sorbitan fatty acid ester, polysorbate, sucrose fatty acid ester, polyoxyethylene, hardened castor oil, polyvinyl pyrrolidone, magnesium stearate, light anhydrous silicic acid, talc, vegetable oil, benzyl alcohol, acacia, propylene glycol, polyalkylene glycol, cyclodextrin and hydroxypropylcyclodextrin.

The dosage forms of pharmaceutical compositions prepared by using these adjuvants include solid preparations such as tablets, capsules, granules, powders and suppositories; liquid preparations such as syrups, elixirs and injections; and the like. These preparations may be formulated according to conventional techniques well-known in the field of pharmaceutics. Liquid preparations may be in a form which is dissolved or suspended in water or other suitable medium prior to use. In particular, injections may be in the form of a solution or suspension in physiological saline solution or a glucose solution, or in powder form for reconstitution by dissolution or suspension in physiological saline or a glucose solution prior to use. If desired, such injections may contain buffer agents and/or preservatives.

As preparations for oral administration, such formulation forms, besides ordinary tablets, capsules, granules, powders and the like, aerosols or dry powders for inhalation, elixirs containing spices or coloring agents or suspensions may be employed.

In these pharmaceutical compositions, a compound in accordance with the present invention may be present at a ratio of from 1.0 to 100% by weight, preferably 1.0 to 60% by weight, based on the total weight of the composition. These pharmaceutical compositions may additionally contain other therapeutically effective compounds.

When the compounds of the present invention are used as drugs, their dosage level and dosage schedule may vary according to the sex, age and body weight of the patient, the severity of symptoms, the type and range of the desired therapeutic effect, and the like. Generally for oral administration, they are preferably administered in a daily dose of 0.1 to 100 mg/kg for adults and this daily dose may be given at a time or in several divided doses. For parenteral administration, they are preferably administered in a daily dose of 0.001 to 10 mg/kg for adults and this daily dose may be given at a time or in several divided doses.

Hereinafter the present invention is more specifically explained with reference to working examples, it being understood that the examples are in no way limitative of the scope of the invention.

EXAMPLE 1

(2R)-N-[1-(4-methyl-3-pentenyl)piperidin-4-yl]-2-[(1R)-3,3-difluorocyclopentyl]-2-hydroxy-2-phenylacetamide Structural formula

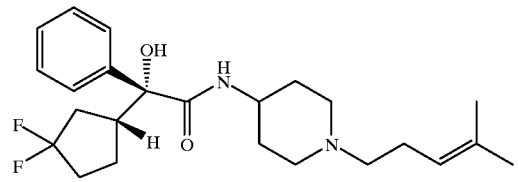

Step 1. Synthesis of 1-(4-methyl-3-pentenyl)-4-piperidone

To a solution of 2.5 g of 4-piperidone monohydrochloride monohydrate in 150 ml of acetonitrile, 11 g of potassium carbonate, 2.62 g of 5-bromo-2-methyl-2-pentene and 800 mg of potassium iodide were added sequentially, and the mixture was heated under reflux for 3 hours. The reaction mixture was diluted with ethyl acetate, washed with water and then with brine, and dried over anhydrous magnesium sulfate. Distilling the solvent off under reduced pressure, 2.24 g of the title compound was obtained as a white solid.

Step 2. Synthesis of 4-amino-1-(4-methyl-3-pentenyl) piperidine

To a solution of 2.2 g of 1-(4-methyl-3-pentenyl)-4-piperidone in 60 ml of methanol, 1.1 g of ammonium acetate and 860 mg of sodium cyanoborohydride were added sequentially, at room temperature, followed by stirring overnight at same temperature. Distilling the methanol off under reduced pressure, the pH of the reaction media was adjusted to 3 with 1N hydrochloric acid, followed by washing with diethyl ether. The aqueous layer was basified with 1N aqueous sodium hydroxide solution and extracted with chloroform. The organic layer was washed with water and then brine, and dried over anhydrous magnesium sulfate. Distilling the solvent off under reduced pressure, 1.9 g of the title compound was obtained as a colorless oil.

Step 3. Synthesis of (2R)-N-[1-(4-methyl-3-pentenyl) piperidin-4-yl]-2-[(1R)-3,3-difluorocyclopentyl]-2-hydroxy-2-phenylacetamide To a solution of 75 mg of (2R)-[(1R)-3,3-difluorocyclopentyl]-2-hydroxy-2-phenylacetic acid in 3 ml of N,N-dimethylformamide, 55 mg of 1,1'-carbonyldiimidazole was added at room temperature, followed by stirring for 2 hours at the same temperature. Then 60 mg of 4-amino-1-(4-methyl-3-pentenyl)piperidine and 5 mg of 4-dimethylaminopyridine were added sequentially, followed by stirring overnight at room temperature. The reaction mixture was diluted with diethyl ether, washed with saturated aqueous sodium bicarbonate solution, water and brine, and dried over anhydrous magnesium sulfate. Distilling the solvent off under reduced pressure, the resulting residue was purified by preparative thin layer chromatography [Kieselgel™ 60F$_{254}$, Art 5744 (manufactured by E. Merck); chloroform/methanol=10/1], to provide 23 mg of the title compound as an oil.

$^1$H-NMR (CDCl$_3$, δ ppm): 1.32–1.50 (2H, m), 1.60 (3H, s), 1.68 (3H, s) 1.58–2.34 (12H, m), 2.43–2.49 (1H, m) 2.73–2.82 (3H, m), 3.23–3.36 (1H, m), 3.48 (1H, brs), 3.62–3.73 (1H, m), 5.03–5.08 (1H, m), 6.29–6.33 (1H, m), 7.25–7.39 (3H, m), 7.54–7.57 (2H, m)

low resolution FAB-MS (m/e, (C$_{24}$H$_{34}$F$_2$N$_2$O$_2$+H)$^+$): 421.

EXAMPLE 2

(2R)-N-[1-(4-methyl-3-pentenyl)piperidin-4-yl]-2-[(1S)-3,3-difluorocyclopentyl]-2-hydroxy-2-phenylacetamide Structural formula

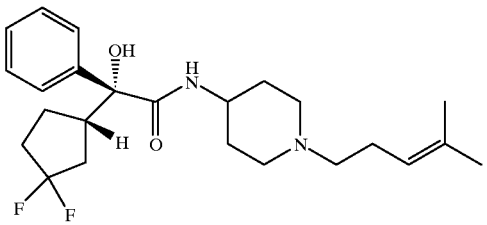

The title compound was prepared in the same manner as described in step 3 of Example 1 using (2R)-[(1S)-3,3-difluorocyclopentyl]-2-hydroxy-2-phenylacetic acid.

$^1$H-NMR (CDCl$_3$, δ ppm): 1.60 (3H, s), 1.68 (3H, s), 1.35–2.48 (15H, m), 2.75–2.86 (3H, m), 3.22–3.36 (1H, m), 3.48 (1H, brs), 3.61–3.76 (1H, m), 5.03–5.08 (1H, m), 6.27 (1H, d, J=8.0 Hz), 7.26–7.40 (3H, m), 7.55–7.58 (2H, m)

low resolution FAB-MS (m/e, (C$_{24}$H$_{34}$F$_2$N$_2$O$_2$+H)$^+$): 421.

EXAMPLE 3

(2R)-N-[1-(4-methyl-3-pentenyl)piperidin-4-yl]-2-[(1S,3S)-3-fluorocyclopentyl]-2-hydroxy-2-phenylacetamide and (2R)-N-[1-(4-methyl-3-pentenyl)piperidin-4-yl]-2-[(1S,3R)-3-fluorocyclopentyl]-2-hydroxy-2-phenylacetamide Structural formulae

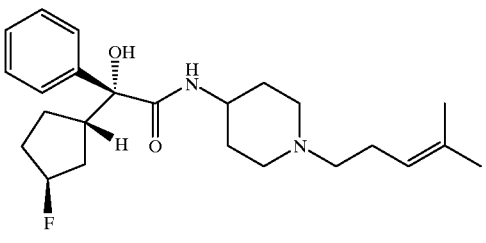

and

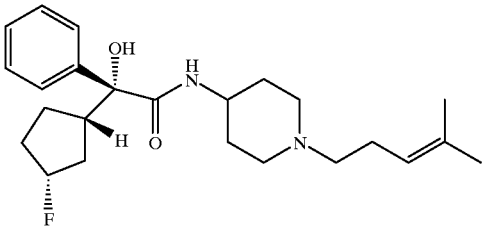

The title compounds were prepared using (2R)-[(1S)-3-fluorocyclopentyl]-2-hydroxy-2-phenylacetic acid, in the same manner as described in step 3 in Example 1, and separated in the final step.

(2R)-N-[1-(4-methyl-3-pentenyl)-piperidin-4-yl]-2-[(1S,3S)-3-fluorocyclopentyl]-2-hydroxy-2-phenylacetamide $^1$H-NMR (CDCl$_3$, δ ppm): 1.60 (3H, s), 1.68 (3H, s), 1.31–2.33 (15H, m), 2.44–2.49 (1H, m), 2.69–2.81 (2H, m), 3.19–3.30 (1H, m), 3.62–3.74 (1H, m), 3.90 (1H, brs), 5.03–5.28 (2H, m), 5.87–5.91 (1H, m), 7.25–7.40 (3H, m), 7.53–7.57 (2H, m)

low resolution FAB-MS (m/e. (C$_{24}$H$_{35}$FN$_2$O$_2$+H)$^+$): 403

(2R)-N-[1-(4-methyl-3-pentenyl)-piperidin-4-yl]-2-[(1S,3R)-3-fluorocyclopentyl]-2-hydroxy-2-phenylacetamide $^1$H-NMR (CDCl$_3$, δ ppm): 1.61 (3H, s) 1.68 (3H, s), 1.37–2.26 (14H, m), 2.32–2.37 (2H, m), 2.75–2.90 (2H, m), 3.43–3.56 (1H, m), 3.62–3.76 (1H, m), 5.04–5.13 (2H, m), 6.91–6.95 (1H, m), 7.23–7.35 (3H, m) 7.67–7.71 (2H, m)

low resolution FAB-MS (m/e, (C$_{24}$H$_{35}$FN$_2$O$_2$+H)$^+$): 403.

EXAMPLE 4

(2R)-N-[1-(4-methyl-3-pentenyl)piperidin-4-yl]-2-[(1R,3S)-3-fluorocyclopentyl]-2-hydroxy-2-phenylacetamide and (2R)-N-[1-(4-methyl-3-pentenyl)piperidin-4-yl]-2-[(1R,3R)-3-fluorocyclopentyl]-2-hydroxy-2-phenylacetamide Structural formulae

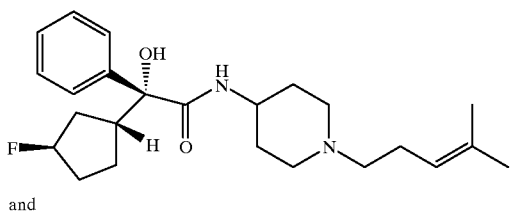

and

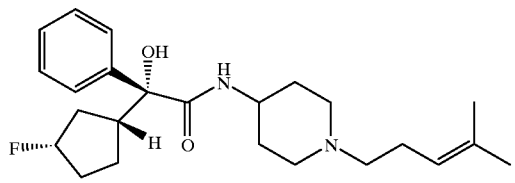

The title compounds were prepared using (2R)-[(1R)-3-fluorocyclopentyl]-2-hydroxy-2-phenylacetic acid, in the same manner as described in step 3 in Example 1, and separated in the final step.

(2R)-N-[1-(4-methyl-3-pentenyl)piperidin-4-yl]-2-[(1R,3S)-3-fluorocyolopentyl]-2-hydroxy-2-phenylacetamide $^1$H-NMR (CDCl$_3$, δ ppm): 1.60 (3H, s) 1.70 (3H, s), 1.38–2.17 (14H, m), 2.27–2.32 (2H, m), 2.70–2.81 (2H, m), 3.19–3.32 (1H, m), 3.63–3.74 (1H, m), 3.93 (1H, brs), 5.00–5.21 (2H, m), 5.96–6.02 (1H, m), 7.26–7.38 (3H, m), 7.55–7.58 (2H, m)

low resolution FAB-MS (m/e, (C$_{24}$H$_{35}$FN$_2$O$_2$+H)$^+$): 403

(2R)-N-[1-(4-methyl-3-pentenyl)piperidin-4-yl]-2-[(1R,3R)-3-fluorocyclopentyl]-2-hydroxy-2-phenylacetamide $^1$H-NMR (CDCl$_3$, δ ppm) 1.60 (3H, s), 1.68 (3H, s), 1.38–2.32 (6H, m) 2.74–2.88 (2H, m), 3.41–3.52 (1H, m), 3.63–3.74 (1H, m), 5.02–5.21 (2H, m), 6.90 (1H, d, J=8.2 Hz), 7.23–7.35 (3H, m), 7.66–7.69 (2H, m)

low resolution FAB-MS (m/e, (C$_{24}$H$_{35}$FN$_2$O$_2$+H)$^+$) 403.

EXAMPLE 5

N-[1-[(3Z)-4-trifluoromethyl-3-pentenyl]piperidin-4-yl]-2-cyclopentyl-2-hydroxy-2-phenylacetamide Structural formula

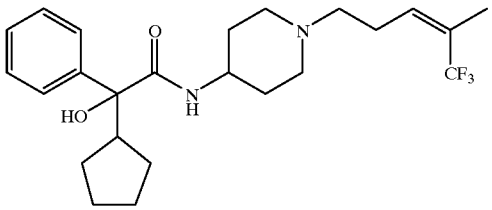

Step 1. Synthesis of N-(piperidin-4-yl)-2-cyclopentyl-2-hydroxy-2-phenylacetamide To a solution of 3.51 g of 2-cyclopentyl-2-hydroxy-2-phenylacetic acid in 40 ml of N,N-dimethylformamide, 2.63 g of 1,1'-carbonyldiimidazole was added and stirred at room temperature for 2 hours. To the reaction mixture 3.96 g of 4-amino-1-(t-butoxycarbonyl)piperidine monohydrochloride, 200 mg of 4-dimethylaminopyridine and 6.9 ml of diisopropylethylamine were added, followed by stirring overnight at room temperature. Saturated aqueous sodium bicarbonate solution was added to the reaction mixture followed by an extraction with diethyl ether. The organic layer was washed with brine and dried over anhydrous sodium sulfate. Distilling the solvent off under reduced pressure, the resultant residue was purified by silica gel column chromatography (developing solvent: hexane/ethyl acetate=3/1) to provide 2.84 g of a white solid. The solid was dissolved in 30 ml of 10% hydrochloric acid-methanol, and stirred overnight at room temperature. Distilling the methanol off under reduced pressure, the residue was diluted with water and washed with diethyl ether. The aqueous layer was made basic with sodium hydroxide and extracted with chloroform. The organic layer was washed with water and then with brine, and dried over anhydrous magnesium sulfate. Distilling the solvent off under reduced pressure, 2.15 g of the title compound was obtained as a white solid.

Step 2. Synthesis of (3Z)-4-trifluoromethyl-3-pentenyl t-butyldiphenylsilyl ether To a solution of 2.94 g of (3-t-butyldiphenylsilyl oxypropyl)triphenylphosphoniumbromide in 40 ml of tetrahydrofuran, 2.5 ml of 1.7 M hexane solution of n-butyllithium was added dropwise at −78° C. The temperature was raised to −20° C. After stirring for an hour at said temperature, reaction mixture was cooled to −78° C. into which 0.5 ml of trifluoroacetone was added dropwise, followed by stirring overnight while raising the temperature to room temperature. The reaction liquid was diluted with hexane, washed with 10% hydrochloric acid, water and then brine, and dried over anhydrous magnesium sulfate. Distilling the solvent off under reduced pressure, resulting residue was purified by silica gel column chromatography (developing solvent: hexane/ethyl acetate=9/1) to provide 1.44 g of the title compound.

Step 3. Synthesis of (3Z)-4-trifluoromethyl-3-pentenol

To a solution of 1.44 g of (3Z)-4-trifluoromethyl-3-pentenyl t-butyl-diphenylsilyl ether in 8 ml of tetrahydrofuran, 4.4 ml of 1.0 M solution of tetrabutylammonium fluoride in tetrahydrofuran was added, followed by stirring for 2 hours at room temperature. The reaction mixture was diluted with diethyl ether, washed with water and then brine, and dried over anhydrous magnesium sulfate. Distilling the solvent off under reduced pressure, the residue was purified by silica gel column chromatography (developing solvent: ethyl acetate) to provide 414 mg of the title compound.

Step 4. Synthesis of (3Z)-4-trifluoromethyl-3-pentenyl p-toluenesulfonate

To a solution of 414 mg of (3Z)-4-trifluoromethyl-3-pentenol in 6 ml of pyridine, 565 mg of p-toluenesulfonyl chloride was added under cooling with ice, followed by stirring for 16 hours at room temperature. The reaction mixture was diluted with diethyl ether, washed with water and then brine, and dried over anhydrous magnesium sulfate. Distilling the solvent off under reduced pressure, the residue was purified by silica gel column chromatography (developing solvent: hexane/ethyl acetate=9/1) to provide 412 mg of the title compound.

Step 5. Synthesis of N-[1-[(3Z)-4-trifluoromethyl-3-pentenyl]piperidin-4-yl]-2-cyclopentyl-2-hydroxy-2-phenylacetamide To a solution of 77 mg of N-(piperidin-4-yl)-2-cyclopentyl-2-hydroxy-2-phenylacetamide in 3 ml of N,N-dimethylformamide, 74 mg of (3Z)-4-trifluoromethyl-3-pentenyl p-toluenesulfonate, 102 mg of potassium carbonate and 43 mg of potassium iodide were added by the order stated, followed by 3 hours' heating under reflux. The reaction liquid was diluted with diethyl ether, washed with water and saturated saline solution by the order stated, and dried over anhydrous magnesium sulfate. Distilling the solvent off under reduced pressure, the residue was purified by preparative thin layer chromatography (Kieselgel™ 60F$_{254}$, Art 5744 (Merck) chloroform/methanol=9/1) to provide 27 mg of the title compound as an oily substance.

$^1$H-NMR (CDCl$_3$, δ ppm): 1.12–1.88 (16H, m), 1.83 (3H, s), 2.01–2.13 (2H, m), 2.68–2.80 (2H, m), 2.97–3.10 (1H, m), 3.13 (1H, brs), 3.62–3.76 (1H, m), 5.65–5.72 (1H, m), 6.32 (1H, d, J=8.5 Hz), 7.23–7.36 (3H, m), 7.59 (2H, d, J=7.3 Hz)

low resolution FAB-MS (m/e, (C$_{24}$H$_{33}$F$_3$N$_2$O$_2$+H)$^+$): 439.

EXAMPLE 6

N-[1-[(3Z)-4-fluoromethyl-3-pentenyl]piperidin-4-yl]-2-cyclopentyl-2-hydroxy-2-phenylacetamide Structural formula

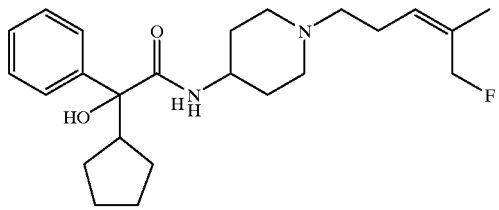

The title compound was prepared by the procedures similar to steps 2–5 of Example 5, using fluoroacetone.

$^1$H-NMR (CDCl$_3$, δ ppm): 1.04–2.16 (14H, m), 1.79 (3H, s), 2.16–2.28 (2H, m), 2.28–2.40 (2H, m), 2.66–2.86 (2H, m) 2.94–3.24 (2H, m), 3.62–3.78 (1H, m), 4.86 (2H, d, J=47.5 Hz), 5.34–5.44 (1H, m), 6.36 (1H, d, J=8.3 Hz), 7.22–7.40 (3H, m), 7.56–7.64 (2H, m)

EXAMPLE 7

N-[1-[(3E)-4-fluoromethyl-3-pentenyl]piperidin-4-yl]-2-cyclopentyl-2-hydroxy-2-phenylacetamide Structural formula

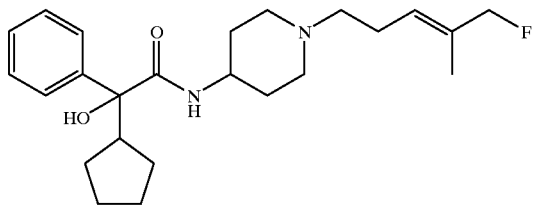

Step 1. Synthesis of (2E)-5-bromo-2-methyl-2-pentenol

To a solution of 681 mg of selenium dioxide in 10 ml of dichloromethane, 2.5 ml of t-butyl peroxide was added at room temperature, stirred for 30 minutes at said temperature, and further 2.0 g of 5-bromo-2-methyl-2-pentene was added, followed by stirring for 2 hours. The reaction mixture was diluted with diethyl ether, washed with aqueous sodium thiosulfate solution, 10% aqueous potassium hydroxide solution, and then with brine, and dried over anhydrous magnesium sulfate. Distilling the solvent off under reduced pressure, the residue was purified by silica gel column chromatography (developing solvent: hexane/ethyl acetate=20/1–4/1) to provide 1.24 g of the title compound.

Step 2. Synthesis of (2E)-5-bromo-2-methyl-2-pentenyl t-butyldimethylsilyl ether To a solution of 300 mg of (2E)-5-bromo-2-methyl-2-pentenol in 10 ml of N,N-dimethylformamide, 302 mg of t-butyldimethylsilyl chloride and 137 mg of imidazole were added, followed by stirring for an hour at room temperature. The reaction liquid was diluted with diethyl ether, washed with water and then with brine, and dried over anhydrous magnesium sulfate. Distilling the solvent off under reduced pressure. 604 mg of the title compound was obtained.

Step 3. Synthesis of N-[1-[(3E)-4-t-butyldimethylsilyloxymethyl-3-pentenyl]piperidin-4-yl]-2-cyclopentyl-2-hydroxy-2-phenylacetamide The title compound was prepared by the method similar to step 5 of Example 5, using (2E)-5-bromo-2-methyl-2-pentenyl t-butyldimethylsilyl ether.

Step 4. Synthesis of N-[1-[(3E)-4-fluoromethyl-3-pentenyl] piperidin-4-yl]-2-cyclopentyl-2-hydroxy-2-phenylacetamide To a solution of 59 mg of tetrabutylammonium-fluoride trihydrate in 3 ml of tetrahydrofuran, 200 mg of molecular sieves 4A, 31 mg of N-[1-[(3E)-4-t-butyldimethylsilyloxymethyl-3-pentenyl]piperidin-4-yl]-2-cyclopentyl-2-hydroxy-2-phenylacetamide and 22 mg of p-toluenesulfonylfluoride were added sequentially, followed by overnight heating under reflux at 80° C. After removal of the insoluble material by filtration, the solvent was distilled off under reduced pressure. The remaining residue was purified by preparative thin layer chromatography [Kieselgel™ 60F$_{254}$, Art 5744 (Merck); chloroform/methanol=20/1], to provide 11 mg of the title compound as an oily substance.

$^1$H-NMR (CDCl$_3$ δ ppm): 1.10–1.76 (10H, m), 1.70 (3H, s), 1.76–1.95 (2H, m), 1.95–2.42 (6H, m), 2.72–2.88 (2H, m), 2.94–3.24 (2H, m), 3.62–3.78 (1H, m), 4.69 (2H, d, J=47.8 Hz), 5.44–5.54 (1H, m) 6.37 (1H, d, J=8.0 Hz), 7.22–7.40 (3H, m), 7.56–7.64 (2H, m)

low resolution FAB-MS (m/e, (C$_{24}$H$_{35}$FN$_2$O$_2$+H)$^+$): 403

EXAMPLE 8

(2R)-N-(1-cycloheptylmethylpiperidin-4-yl)-2-[(1R)-3,3-difluorocyclopentyl]-2-hydroxy-2-phenylacetamide Structural formula

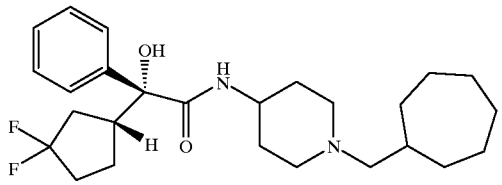

The title compound was prepared by a method similar to the steps 1 and 5 of Example 5, using (2R)-2-[(1R)-3,3-difluorocyclopentyl]-2-hydroxy-2-phenylacetic acid and cycloheptylmethyl methanesulfonate.

$^1$H-NMR (CDCl$_3$, δ ppm): 1.03–2.27 (27H, m), 2.63–2.71 (2H, m), 3.21–3.33 (1H, m), 3.49 (1H, brs), 3.61–3.72 (1H, m), 6.23 (1H, d, J=8.3 Hz), 7.27–7.39 (3H, m), 7.53–7.57 (2H, m)

low resolution FAB-MS (m/e, (C$_{26}$H$_{38}$F$_2$N$_2$O$_2$+H)$^+$): 449.

EXAMPLE 9

(2R)-N-[1-[(3E)-4-fluoromethyl-3-pentenyl]-piperidin-4-yl]-2-[(1R)-3,3-difluorocyclopentyl]-2-hydroxy-2-phenylacetamide Structural formula

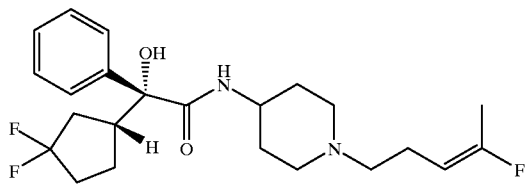

The title compound was prepared by a method similar to Example 7, using (2R)-2-[(1R)-3,3-difluorocyclopentyl]-2-hydroxy-2-phenylacetic acid.

$^1$H-NMR (CDCl$_3$, δ ppm): 1.34–1.52 (2H, m), 1.69 (3H, s), 1.75–2.31 (12H, m), 2.31–2.46 (2H, m), 2.72–2.86 (2H, m), 3.24–3.38 (1H, m), 3.43 (1H, brs), 3.62–3.78 (1H, m), 4.69 (2H, d, J=47.8 Hz), 5.42–5.52 (1H, m), 6.34 (1H, d, J=7.9 Hz), 7.24–7.42 (3H, m), 7.52–7.60 (2H, m)

low resolution FAB-MS (m/e, (C$_{24}$H$_{33}$F$_3$N$_2$O$_2$+H)$^+$): 439.

EXAMPLE 10

(2R)-N-[1-(6-methylpyridin-2-ylmethyl)piperidin-4-yl]-2-[(1R)-3,3-difluorocyclopentyl]-2-hydroxy-2-phenylacetamide Structural formula

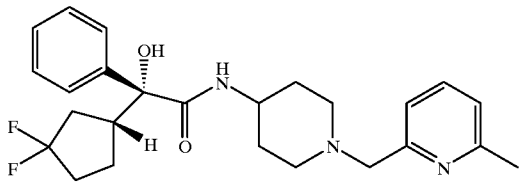

Step 1. Synthesis of (2R)-N-(piperidin-4-yl)-2-[(1R)-3,3-difluorocyclopentyl]-2-hydroxy-2-phenylacetamide The title compound was prepared by a method similar to the step 1 of Example 5, using (2R)-2-[(1R)-3,3-difluorocyclopentyl]-2-hydroxy-2-phenylacetic acid.

Step 2. Synthesis of (2R)-N-[1-(6-methylpyridin-2-ylmethyl)piperidin-4-yl]-2-[(1R)-3,3-difluorocyclopentyl]-2-hydroxy-2-phenylacetamide To a solution of 17 mg of (2R)-N-(piperidin-4-yl)-2-[(1R)-3,3-difluorocyclopentyl]-2-hydroxy-2-phenylacetamide in 2 ml of tetrahydrofuran, 3 μl of acetic acid, 12 mg of 6-methylpyridine-2-carbaldehyde and 21 mg of sodium triacetoxyborohydride were added sequentially at room temperature, and stirred overnight at the same temperature. The reaction mixture was diluted with ethyl acetate, washed with brine and dried over anhydrous magnesium sulfate. Distilling the solvent off under reduced pressure, the residue was purified by preparative thin layer chromatography (Kieselgel™ 60$F_{254}$, Art 5744 (Merck) chloroform/methanol=10/1) to provide 9 mg of the title compound as a solid substance.

$^1$H-NMR (CDCl$_3$, δ ppm): 1.35–1.50 (2H, m), 1.72–2.23 (10H, m), 2.53 (3H, s), 2.70–2.80 (2H, m), 3.21–3.35 (1H, m), 3.59 (2H, s), 3.60–3.78 (1H, m), 6.31 (1H, d, J=8.5 Hz), 7.02 (1H, t J=7.6 Hz) 7.18 (1H, d, J=7.6 Hz), 7.28–7.39 (3H, m), 7.50 (1H, d, J=7.6 Hz), 7.53–7.59 (2H, m)

EXAMPLE 11

(2R)-N-[1-(3-thienylmethyl)piperidin-4-yl]-2-[(1R)-3,3-difluorocyclopentyl]-2-hydroxy-2-phenylacetamide Structural formula

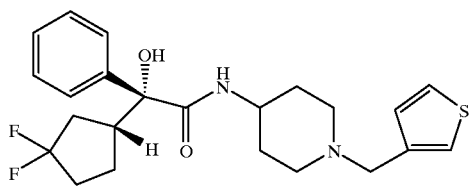

The title compound was prepared by a method similar to the step 2 of Example 10 using thiophene-3-aldehyde.

$^1$H-NMR (CDCl$_3$, δ ppm): 1.30–1.50 (2H, m), 1.56–2.30 (10H, m), 2.66–2.82 (2H, m), 3.22–3.37 (1H, m), 3.40 (1H, s), 3.49 (2H, s), 3.61–3.78 (1H, m), 6.25 (1H, d, J=8.2 Hz), 7.02 (1H, dd, J=1.1 Hz, 7.6 Hz), 7.06–7.12 (1H, m), 7.22–7.42 (4H, m), 7.50–7.60 (2H, m)

low resolution FAB-MS (m/e, (C$_{23}$H$_{28}$F$_2$N$_2$O$_2$S+H)$^+$): 435.

EXAMPLE 12

(2R)-N-[1-(3-furylmethyl)piperidin-4-yl]-2-[(1R)-3,3-difluorocyclopentyl]-2-hydroxy-2-phenylacetamide Structural formula

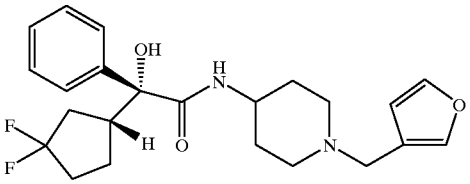

The title compound was prepared by a method similar to the step 2 of Example 10, using furan-3-aldehyde.

$^1$H-NMR (CDCl$_3$, δ ppm): 1.32–1.47 (2H, m), 1.73–2.27 (10H, m), 2.70–2.78 (2H, m), 3.24–3.35 (1H, m), 3.33 (2H, s), 3.42 (1H, s), 3.62–3.75 (1H, m), 6.26 (1H, d, J=7.2 Hz), 6.34 (1H, s), 7.27–7.40 (5H, m), 7.52–7.57 (2H, m)

low resolution FAB-MS (m/e. (C$_{23}$H$_{28}$F$_2$N$_2$O$_3$+H)$^+$) 419.

EXAMPLE 13

(2R)-N-[1-(2-furylmethyl)piperidin-4-yl]-2-[(1R)-3,3-difluorocyclopentyl]-2-hydroxy-2-phenylacetamide Structural formula

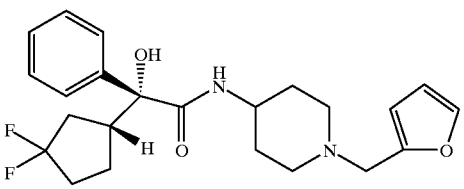

The title compound was prepared by a method similar to the step 2 of Example 10, using furan-2-aldehyde.

$^1$H-NMR (CDCl$_3$, δ ppm) 1.35–1.49 (2H, m), 1.73–2.25 (10H, m), 2.70–2.80 (2H, m), 3.23–3.35 (1H, m), 3.48 (1H, s), 3.49 (2H, s), 3.61–3.73 (1H, m), 6.17 (1H, d, J=3.0 Hz), 6.27–6.31 (2H, m), 7.27–7.38 (4H, m), 7.52–7.56 (2H, m)

low resolution FAB-MS (m/e, (C$_{23}$H$_{28}$F$_2$N$_2$O$_3$+H)$^+$): 419.

EXAMPLE 14

(2R)-N-[1-(2-pyridylmethyl)piperidin-4-yl]-2-[(1R)-3,3-difluorocyclopentyl]-2-hydroxy-2-phenylacetamide Structural formula

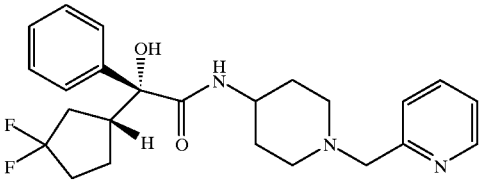

The title compound was prepared by a method similar to the step 2 of Example 10, using pyridine-2-aldehyde.

$^1$H-NMR (CDCl$_3$, δ ppm) 1.39–1.52 (2H, m), 1.75–2.25 (10H, m), 2.70–2.80 (2H, m), 3.24–3.36 (1H, m), 3.58 (1H, s), 3.61 (2H, s), 3.67–3.77 (1H, m), 6.32 (1H, d, J=7.8 Hz), 7.15 (1H, ddd, J=1.2 Hz, 4.8 Hz, 7.6 Hz), 7.27–7.39 (4H, m), 7.53–7.57 (2H, m), 7.63 (1H, td, J=1.8 Hz, 7.6 Hz), 8.52 (1H, ddd, J=1.2 Hz, 1.8 Hz, 3.0 Hz)

low resolution FAB-MS (m/e, $(C_{24}H_{29}F_2N_3O_2+H)^+$) 430.

EXAMPLE 15

(2R)-N-[1-(3-methoxybenzyl)piperidin-4-yl]-2-[(1R)-3,3-difluorocyclopentyl]-2-hydroxy-2-phenylacetamide Structural formula

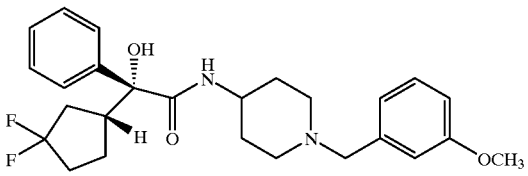

To a solution of 71 mg of (2R)-N-(piperidin-4-yl)-2-[(1R)-3,3-difluorocyclopentyl]-2-hydroxy-2-phenylacetamide in 2 ml of N,N-dimethylformamide, 74 mg of 3-methoxybenzyl chloride and 80 mg of potassium carbonate were added at room temperature, followed by stirring for about 12 hours. The reaction mixture was diluted with diethyl ether, washed with water and then brine, and dried over anhydrous magnesium sulfate. Distilling the solvent off under reduced pressure, the residue was purified by preparative thin layer chromatography (Kieselgel™ 60F$_{254}$, Art 5744 (Merck) chloroform/methanol=9/1) to provide 75 mg of the title compound as a white solid.

$^1$H-NMR (CDCl$_3$, δ ppm): 1.32–1.54 (2H, m), 1.65–2.30 (10H, m), 2.68–2.85 (2H, m), 3.21–3.39 (1H, m), 3.42 (1H, s) 3.45 (2H, s), 3.62–3.78 (1H, m), 3.80 (3H, s), 6.27 (1H, d, J=8.2 Hz), 6.76–6.83 (1H, m), 6.84–6.90 (2H, m), 7.21 (1H, t, J=8.0 Hz), 7.24–7.40 (3H, m), 7.51–7.59 (2H, m)

low resolution FAB-MS (m/e, $(C_{26}H_{32}F_2N_2O_3+H)^+$): 459.

EXAMPLE 16

(2R)-N-(1-benzylpiperidin-4-yl)-2-[(1R)-3,3-difluorocyclopentyl]-2-hydroxy-2-phenylacetamide Structural formula

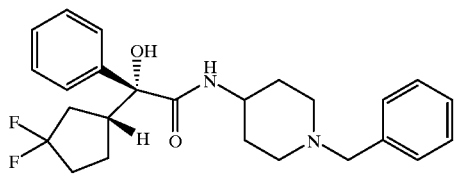

The title compound was prepared in the same manner as described in Example 15 using benzyl bromide.

$^1$H-NMR (CDCl$_3$, δ ppm): 1.35–1.52 (2H, m), 1.70–2.23 (10H, m), 2.70–2.81 (2H, m), 3.22–3.34 (1H, m), 3.41 (1H, s) 3.48 (2H, s), 3.60–3.80 (1H, m), 6.27 (1H, d, J=8.0 Hz), 7.24–7.39 (8H, m), 7.54–7.56 (2H, m)

low resolution FAB-MS (m/e, $(C_{25}H_{30}F_2N_2O_2+H)^+$): 429.

EXAMPLE 17

(2R)-N-[1-(3-fluorobenzyl)piperidin-4-yl]-2-[(1R)-3,3-difluorocyclopentyl]-2-hydroxy-2-phenylacetamide Structural formula

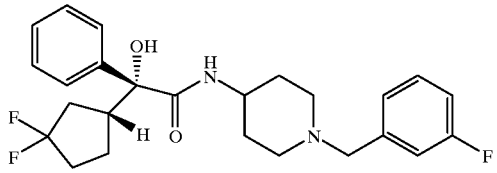

The title compound was prepared in the same manner as described in Example 15 using 3-fluorobenzyl chloride.

$^1$H-NMR (CDCl$_3$, δ ppm): 1.34–1.52 (2H, m), 1.52–2.30 (10H, m), 2.65–2.80 (2H, m), 3.22–3.38 (1H, m), 3.40 (1H, s) 3.72 (2H, s), 3.60–3.80 (1H, m), 6.28 (1H, d, J=7.7 Hz), 6.88–6.97 (1H, m), 7.00–7.10 (2H, m), 7.20–7.42 (4H, m), 7.51–7.60 (2H, m)

low resolution FAB-MS (m/e, $(C_{25}H_{29}F_3N_2O_2+H)^+$): 447.

EXAMPLE 18

(2R)-N-[1-(3-chlorobenzyl)piperidin-4-yl]-2-[(1R)-3,3-difluorocyclopentyl]-2-hydroxy-2-phenylacetamide Structural formula

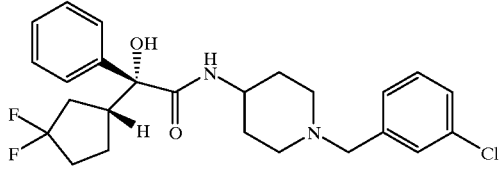

The title compound was prepared in the same manner as described in Example 15 using 3-chlorobenzyl chloride.

$^1$H-NMR (CDCl$_3$, δ ppm): 1.33–1.50 (2H, m), 1.60–2.25 (10H, m), 2.67–2.77 (2H, m), 3.24–3.38 (1H, m), 3.44 (2H, s) 3.63–3.76 (1H, m), 6.29 (1H, d, J=8.0 Hz), 7.13–7.40 (7H, m), 7.53–7.57 (2H, m)

low resolution FAB-MS (m/e, $(C_{25}H_{29}ClF_2N_2O_2+H)^+$): 463.

EXAMPLE 19

(2R)-N-[1-(2-thienylmethyl)piperidin-4-yl]-2-[(1R)-3,3-difluorocyclopentyl]-2-hydroxy-2-phenylacetamide Structural formula

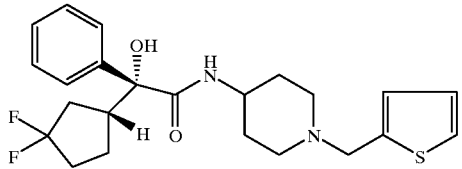

The title compound was prepared in the same manner as described in Example 15 using 2-thienylmethyl chloride.

$^1$H-NMR (CDCl$_3$, δ ppm): 1.32–1.50 (2H, m), 1.52–2.30 (10H, m), 2.70–2.82 (2H, m), 3.22–3.36 (1H, m), 3.41 (1H, s) 3.62–3.76 (1H, m), 3.68 (2H, s), 6.26 (1H, d, J=7.9 Hz), 6.87 (1H, dd, J=3.2 Hz, 4.8 Hz), 6.92 (1H, dd, J=3.2 Hz, 4.8 Hz) 7.21 (1H, dd, J=1.5 Hz, 4.8 Hz), 7.24–7.40 (3H, m), 7.50–7.58 (2H, m)

low resolution FAB-MS (m/e, $(C_{23}H_{28}F_2N_2O_2S+H)^+$): 435.

EXAMPLE 20

(2R)-N-[1-(6-aminopyridin-2-ylmethyl)piperidin-4-yl]-2-[(1R)-3,3-difluorocyclopentyl]-2-hydroxy-2-phenylacetamide dihydrochloride Structural formula

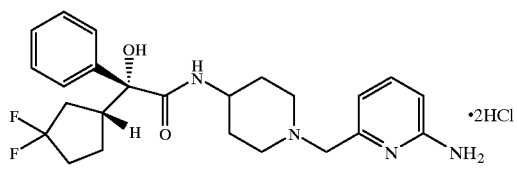

The compound of Example 20 was prepared by the following methods 1, 2 and 3.

Method 1:

Step 1. Synthesis of 6-tert-butyldiphenylsilyloxymethylpyridine-2-carboxylic acid To a solution of 1.8 g of ethyl 6-hydroxymethylpyridine-2-carboxylate in 55 ml of N,N-dimethylformamide, 1.4 g of imidazole and 3.9 g of tert-butyldiphenylsilane chloride were added under cooling with ice, sequentially, followed by stirring for 12 hours at room temperature. The reaction mixture was diluted with ethyl acetate, washed with saturated sodium bicarbonate solution, water and then brine, and dried over anhydrous magnesium sulfate. Distilling the solvent off under reduced pressure, the residue was dissolved in 60 ml of methanol. To the solution 7.5 ml of 4N aqueous sodium hydroxide solution was added, stirred for 20 hours at room temperature and for further 2 hours at 60° C. Distilling the methanol off under reduced pressure, the residue was made acidic with 1N hydrochloric acid. The system was extracted with chloroform, washed with water and then brine, and dried over anhydrous magnesium sulfate. Distilling the solvent off under reduced pressure, the resulting residue was purified by silica gel column chromatography (developing solvent: hexane/ethyl acetate=4/1) to provide 895 mg of the title compound as a white solid.

Step 2. Synthesis of 6-tert-butyloxycarbonylaminopyridin-2-ylmethyl tert-butyldiphenylsilyl ether To a solution of 890 mg of the 6-tert-butyldiphenylsilyloxymethylpyridine-2-carboxylic acid as obtained in above step 1 in 30 ml of toluene, 0.63 ml of triethylamine, 3.2 ml of tert-butanol and 887 mg of diphenylphosphorylazide were added sequentially at room temperature, followed by heating for 16 hours at 100° C. under stirring. The reaction mixture was diluted with ethyl acetate, washed with saturated aqueous sodium bicarbonate solution, 10% aqueous citric acid solution, water and then brine, and dried over anhydrous magnesium sulfate. After the solvent was distilled off under reduced pressure, the resulting residue was purified by silica gel column chromatography (developing solvent: hexane/ethyl acetate=4/1) to provide 863 mg of the title compound as an oily substance.

Step 3. Synthesis of 6-tert-butyloxycarbonylaminopyridine-2-methanol

The title compound was prepared in the same manner as described in the step 3 of Example 5 using the 6-tert-butyloxycarbonylaminopyridin-2-ylmethyl tert-butyldiphenylsilyl ether as obtained in above step 2.

Step 4. Synthesis of 6-tert-butyloxycarbonylaminopyridin-2-ylmethyl methanesulfonate To a solution of 61 mg of the 6-tert-butyloxycarbonylaminopyridine-2-methanol as obtained in above step 3 in 2 ml of chloroform, 0.19 ml of triethylamine and 0.032 ml of methanesulfonyl chloride were added under cooling with ice, followed by stirring for an hour at the same temperature. The reaction liquid was diluted with ethyl acetate, washed with saturated aqueous sodium bicarbonate solution, water and brine by the order stated and dried over anhydrous magnesium sulfate. The solvent was removed under reduced pressure to give 124 mg of the title compound as an oil.

Step 5. Synthesis of (2R)-N-[1-(6-tert-butyloxycarbonylaminopyridin-2-ylmethyl)piperidin-4-yl]-2-[(1R)-3,3-difluorocyclopentyl]-2-hydroxy-2-phenylacetamide The title compound was prepared in the same manner as described in Example 15 using the 6-tert-butyloxycarbonylaminopyridin-2-ylmethyl methanesulfonate as obtained in the step 4 above.

Step 6. Synthesis of (2R)-N-[1-(6-aminopyridin-2-ylmethyl)piperidin-4-yl]-2-[(1R)-3,3-difluorocyclopentyl]-2-hydroxy-2-phenylacetamide The title compound was obtained as a white solid, upon treating the (2R)-N-[1-(6-tert-butyloxycarbonylaminopyridin-2-ylmethyl)piperidin-4-yl]-2-[(1R)-3,3-difluorocyclophenyl]-2-hydroxy-2-phenylacetamide as obtained in above step 5 with hydrochloric acid according to usual manner.

$^1$H-NMR (CD$_3$OD, δ ppm) 1.76–2.14 (10H, m), 3.20–3.63 (5H, m), 3.85–4.00 (1H, m), 4.44 (2H, s), 7.07–7.34 (2H, m), 7.25–7.34 (3H, m), 7.58–7.60 (2H, m), 7.89–7.94 (1H, m)

low resolution FAB-MS (m/e, $(C_{24}H_{30}F_2N_4O_2+H)^+$): 445.

Method 2:

Step 1. Synthesis of ethyl 6-tert-butyloxycarbonylaminopyridine-2-carboxylate

The title compound was prepared in the same manner described in the step 2 of above method 1, using 6-ethoxycarbonylpyridine-2-carboxylic acid.

Step 2. Synthesis of 6-tert-butyloxycarbonylaminopyridine-2-methanol

To a solution of 500 mg of calcium chloride in 10 ml of ethanol, 150 mg of sodium borohydride was added under cooling with ice, followed by stirring for 15 minutes at the same temperature. To the reaction mixture 1.1 g of the ethyl 6-tert-butyloxycarbonylaminopyridine-2-carboxylate as obtained in above step 1 was added and stirred for 13 hours at room temperature. The ethanol was distilled off under reduced pressure, and the residue was suspended in chloroform-water mixture to be removed of insoluble material. The organic layer was washed with water and then brine and dried over anhydrous magnesium sulfate. Thus 996 mg of the title compound was obtained as a light yellow oil.

Step 3. Synthesis of 4-tert-butyloxycarbonylamino-1-(6-tert-butyloxycarbonyaminopyridin-2-ylmethyl)piperidine The title compound was prepared by a method similar to the steps 4 to 5 of above production method 1 using the 6-tert-butyloxycarbonylaminopyridine-2-methanol as obtained in the above step 2 and 4-tert-butyloxycarbonylaminopiperidine.

Step 4. Synthesis of (2R)-N-[1-(6-aminopyridin-2-ylmethyl)piperidin-4-yl]-2-[(1R)-3,3-difluorocyclopentyl]-2-hydroxy-2-phenylacetamide 163 mg of the 4-tert-butyloxycarbonyl-amino-1-(6-tert-butyloxycarbonylaminopyridin-2-ylmethyl)piperidine as obtained in above step 3 was dissolved in 5 ml of 10% HCl-methanol solution, followed by stirring for 13 hours at 40° C. Distilling the methanol off under reduced pressure, the remaining residue was suspended in 15 ml of chloroform, to which 0.16 ml of triethylamine, 86 mg of (2R)-2-[(1R)-3,3-difluorocyclopentyl]-2-hydroxy-2-phenylacetic acid, 114 mg of hydroxybenzotriazole and 75 mg of 1-ethyl-3-(3-dimethylaminopropyl)carbodiimide were added under cooling with ice sequentially, followed by stirring for 1.5 hours at room temperature. The reaction mixture was diluted with diethyl ether, washed with saturated aqueous sodium bicarbonate solution and then brine, and dried over anhydrous magnesium sulfate. After the solvent was distilled off under reduced pressure, the resulting residue was purified by silica gel column chromatography (developing solvent: chloroform/methanol=50/1 to 20/1) to obtain 101 mg of the title compound as a white solid.

$^1$H-NMR (CDCl$_3$, δ ppm): 1.35–1.51 (2H, m), 1.70–2.25 (10H, m), 2.68–2.80 (2H, m), 3.21–3.35 (1H, m), 3.41 (2H, s), 3.52 (1H, brs), 3.62–3.77 (1H, m), 4.40 (2H, brs), 6.28 (1H, d, J=8.2 Hz), 6.36 (1H, d, J=8.2 Hz), 6.67 (1H, d, J=7.3 Hz), 7.27–7.40 (4H, m), 7.53–7.57 (2H, m)

Step 5. Synthesis of (2R)-N-[1-(6-aminopyridin-2-ylmethyl)piperidin-4-yl]-2-[(1R)-3,3-difluorocyclopentyl]-2-hydroxy-2-phenylacetamide dihydrochloride The title compound was prepared by treating the (2R)-N-[1-(6-aminopyridin-2-ylmethyl)piperidin-4-yl]-2-[(1R)-3,3-difluorocyclopentyl]-2-hydroxy-2-phenylacetamide with hydrochloric acid according to the accepted practice.

Method 3:

Step 1. Synthesis of 2-tert-butyloxycarbonylamino-6-methylpyridine

To a solution of 2 g of 6-methyl-2-aminopyridine in 30 ml of chloroform, 5 g of di-tert-butyloxydicarbonate was added at room temperature. Then the mixture was heated to 70° C., to which 2.5 g of 4-dimethylaminopyridine was added, followed by stirring for 2 hours at the same temperature. After the solvent was distilled off under reduced pressure, the resulting residue was purified by silica gel column chromatography (developing solvent: hexane/ethyl acetate=20/1) to provide 4.1 g of the title compound as a white solid.

Step 2. Synthesis of (2R)-N-[1-(6-aminopyridin-2-ylmethyl)piperidin-4-yl]-2-[(1R)-3,3-difluorocyclopentyl]-2-hydroxy-2-phenylacetamide dihydrochloride To a solution of 100 mg of the 2-tert-butyloxycarbonylamino-6-methylpyridine as obtained in above step 1 in 3 ml of carbon tetrachloride, 90 mg of N-bromosuccinimide and 10 mg of benzoyl peroxide were added sequentially, followed by heating for 6 hours under reflux with stirring. Filtering the insoluble materials off, the solvent was distilled off under reduced pressure. The title compound was prepared by processing the residue by a method similar to the step 5 of method 1 and the steps 4–5 of the method 2.

EXAMPLE 21

(2R)-N-[1-(6-amino-4-methoxypyridin-2-ylmethyl)piperidin-4-yl]-2-[(1R)-3,3-difluorocyclopentyl]-2-hydroxy-2-phenylacetamide dihydrochloride Structural formula

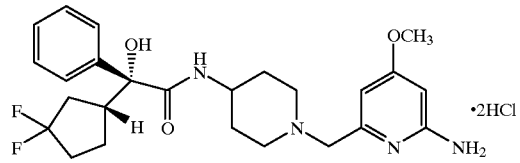

The title compound was prepared by a method similar to Example 20, using ethyl 6-hydroxymethyl-4-methoxypyridine-2-carboxylate.

$^1$H-NMR (CD$_3$OD, δ ppm): 1.69–2.21 (10H, m), 3.10–3.70 (5H, m), 3.83–3.97 (1H, m), 3.98 (3H, s), 4.30–4.46 (2H, m), 6.39–6.47 (1H, m), 6.74–6.89 (1H, m), 7.20–7.38 (3H, m), 7.58 (2H, d, J=6.9 Hz)

low resolution FAB-MS (m/e, (C$_{25}$H$_{32}$F$_2$N$_4$O$_3$+H)$^+$): 475.

EXAMPLE 22

(2R)-N-[1-(3-amino-5-methylbenzyl)piperidin-4-yl]-2-[(1R)-3,3-difluorocyclopentyl]-2-hydroxy-2-phenylacetamide dihydrochloride Structural formula

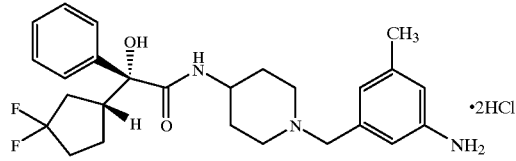

Step 1. Synthesis of N-(tert-butyloxycarbonyl)-3,5-dimethylaniline

To a solution of 1.2 g of 3,5-dimethylaniline in a liquid mixture of 20 ml of dioxane, 10 ml of 10% aqueous sodium hydroxide solution and 2.7 g of di-tert-butyl-dicarbonate were added, followed by heating for 1.5 hours at 100° C. with stirring. The reaction mixture as diluted with diethyl ether, washed with water and then brine, and dried over anhydrous magnesium sulfate. After the solvent was distilled off under reduced pressure, the resulting residue was purified by silica gel column chromatography (developing solvent: hexane/ethyl acetate=9/1) to provide 1.8 g of the title compound as an oil.

Step 2. Synthesis of 3-(tert-butyloxycarbonylamino)-5-methylbenzyl bromide

To a solution of 1.8 g of the N-(tert-butyloxycarbonyl)-3,5-dimethylaniline as obtained in above step 1 in 20 ml of carbon tetrachloride, 1.5 g of N-bromosuccinimide and 53 mg of 2,2'-azobis(isobutyronitrile) were added, followed by heating for 3 hours at 100° C. under stirring. The reaction mixture was diluted with hexane, filtered and the solvent was distilled off under reduced pressure to provide 2.8 g of the title compound as an oil.

Step 3. Synthesis of (2R)-N-[1-(3-amino-5-methylbenzyl)piperidin-4-yl]-2-[(1R)-3,3-difluorocyclopentyl]-2-hydroxy-2-phenylacetamide dihydrochloride The title compound was prepared by a method similar to the steps 5–6 of the production method 1 of Example 20, using the 3-(tert-butyloxycarbonylamino)-5-methylbenzyl bromide as obtained in above step 2.

$^1$H-NMR (CD$_3$OD, δ ppm): 1.66–2.11 (12H, m), 2.99–3.48 (3H, m), 3.26 (3H, s), 3.78–3.98 (1H, m), 4.28 (2H, s), 7.18–7.60 (8H, m)

low resolution FAB-MS (m/e, (C$_{26}$H$_{33}$F$_2$N$_3$O$_2$+H)$^+$): 458.

EXAMPLE 23

(2R)-N-[1-(3-aminobenzyl)piperidin-4-yl]-2-[(1R)-3,3-difluorocyclopentyl]-2-hydroxy-2-phenylacetamide Structural formula

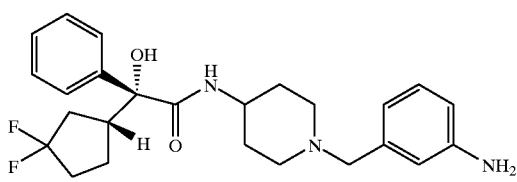

Step 1. Synthesis of (2R)-N-[1-(3-nitrobenzyl)piperidin-4-yl]-2-[(1R)-3, 3-difluorocyclopentyl]-2-hydroxy-2-phenylacetamide The title compound was prepared by a method similar to Example 15, using 3-nitrobenzyl chloride.

Step 2. Synthesis of (2R)-N-[1-(3-aminobenzyl)piperidin-4-yl]-2-[(1R)-3,3-difluorocyolopentyl]-2-hydroxy-2-phenylacetamide 6.5 mg of the (2R)-N-[1-(3-nitrobenzyl)piperidin-4-yl]-2-[(1R)-3,3-difluorocyclopentyl]-2-hydroxy-2-phenylacetamide as obtained in above step 1 was heated to 60° C. together with 2 mg of iron powder in aqueous ethanol. After adding thereto 1 drop of conc. hydrochloric acid, the heating was continued at 100° C. for about 1 hour under stirring. The reaction mixture was made basic with 4N aqueous sodium hydroxide solution and extracted with chloroform. The organic layer was dried over anhydrous sodium sulfate, and the solvent was distilled off under reduced pressure to provide 4.8 mg of the title compound as a white solid.

$^1$H-NMR (CDCl$_3$, δ ppm) 1.30–1.48 (2H, m), 1.50–2.25 (10H, m), 2.68–2.78 (2H, m), 3.24–3.40 (1H, m), 3.38 (2H, s), 3.43 (1H, s), 3.52–3.80 (1H, m), 6.26 (1H, d, J=7.9 Hz), 6.57 (1H, dd, J=1.5 Hz, 7.8 Hz), 6.65 (1H, d, J=1.5 Hz), 6.66 (1H, d, J=7.58 Hz), 7.08 (1H, t, J=7.8 Hz), 7.28–7.39 (3H, m), 7.53–7.57 (2H, m)

low resolution FAB-MS (m/e, (C$_{25}$H$_{31}$F$_2$N$_3$O$_2$+H)$^+$): 444.

EXAMPLE 24

(2R)-N-[1-(2-aminobenzyl)piperidin-4-yl]-2-[(1R)-3,3-difluorocyclopentyl]-2-hydroxy-2-phenylacetamide dihydrochloride Structural formula

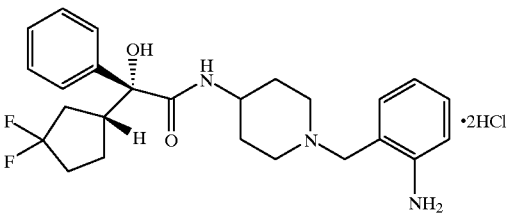

The title compound (free base) was obtained by a method similar to Example 23, using 2-nitrobenzyl chloride, which was treated with hydrochloric and to provide the title dihydrochloride compound.

$^1$H-NMR (CD$_3$OD, δ ppm): 1.50–1.95 (10H, m), 2.92–3.07 (2H, m), 3.07–3.20 (1H, m), 3.24–3.38 (2H, m) 3.67–3.80 (1H, m), 4.15–4.27 (2H, m), 7.05–7.45 (9H, m)

low resolution FAB-MS (m/e, (C$_{25}$H$_{31}$F$_2$N$_3$O$_2$+H)$^+$): 444.

EXAMPLE 25

(2R)-N-[1-(4-aminobenzyl)piperidin-4-yl]-2-[(1R)-3,3-difluorocyclopentyl]-2-hydroxy-2-phenylacetamide Structural formula

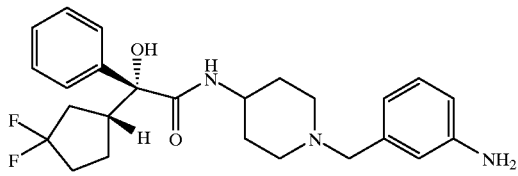

The title compound was prepared by a method similar to Example 23, using 4-nitrobenzyl chloride.

$^1$H-NMR (CDCl$_3$, δ ppm): 1.35–1.52 (2H, m), 1.70–2.23 (10H, m), 2.70–2.82 (2H, m), 3.23–3.35 (1H, m), 3.41 (2H, s), 3.30–3.70 (3H, m), 3.65–3.75 (1H, m), 6.29 (1H, d, J=7.4 Hz), 6.63 (2H, d, J=8.5 Hz), 7.06 (2H, d, J=8.5 Hz), 7.28–7.39 (3H, m), 7.52–7.56 (2H, m)

low resolution FAB-MS (m/e, (C$_{25}$H$_{31}$F$_2$N$_3$O$_2$+H)$^+$): 444.

EXAMPLE 26

(2R)-N-[1-(4-amino-3-methoxybenzyl)piperidin-4-yl]-2-[(1R)-3,3-difluorocyclopentyl]-2-hydroxy-2-phenylacetamide Structural formula

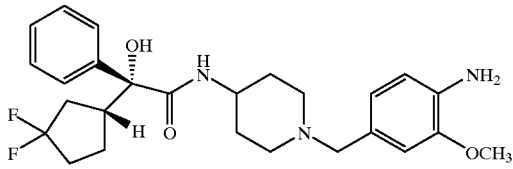

The title compound was prepared by a method similar to Example 23, using 3-methoxy-4-nitrobenzyl chloride.

$^1$H-NMR (CDCl$_3$, δ ppm): 1.35–1.60 (2H, m), 1.70–2.30 (10H, m), 2.70–2.90 (2H, m), 3.22–3.38 (1H, m), 3.44 (2H, s), 3.40–3.60 (1H, m), 3.62–3.85 (3H, m), 3.85 (3H, s), 6.36 (1H, d, J=7.9 Hz), 6.60–6.70 (2H, m), 6.81 (1H, s), 7.24–7.40 (3H, m), 7.51–7.58 (2H, m)

low resolution FAB-MS (m/e, (C$_{26}$H$_{33}$F$_2$N$_3$O$_3$+H)$^+$): 474.

EXAMPLE 27

(2R)-N-[1-(3,5-diaminobenzyl)pipieridin-4-yl]-2-[(1R)-3 3-difluorocyclopentyl]-2-hydroxy-2-phenylacetamide Structural formula

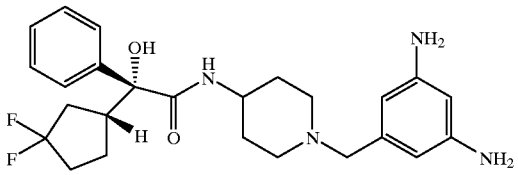

The title compound was prepared by a method similar to Example 23, using 3,5-dinitrobenzyl chloride.

$^1$H-NMR (CDCl$_3$, δ ppm): 1.30–2.20 (12H, m), 2.70–2.80 (2H, m), 3.23–3.36 (1H, m), 3.28 (2H, s), 3.44 (1H, s), 3.60–3.73 (1H, m), 5.93 (1H, t, J=2.0 Hz), 6.07 (2H, d, J=2.0 Hz), 6.23 (1H, d, J=7.5 Hz), 7.29–7.40 (3H, m), 7.53–7.57 (2H, m)

low resolution FAB-MS (m/e, (C$_{25}$H$_{32}$F$_2$N$_4$O$_2$+H)$^+$): 459.

EXAMPLE 28

(2R)-N-[1-(5-methylfuran-2-ylmethyl)piperidin-4-yl]-2-[(1R)-3,3-difluorocyclopentyl]-2-hydroxy-2-phenylacetamide Structural formula

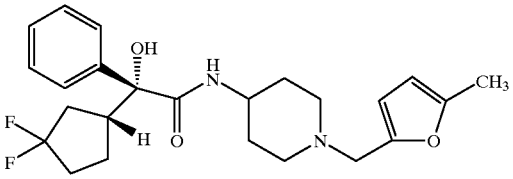

Step 1. Synthesis of 4-(tert-butyloxycarbonylamino)-1-(5-methyl-2-furylmethyl)piperidine To a solution of 200 mg of 4-(tert-butyloxycarbonylamino)piperidine in 5 ml of tetrahydrofuran, 0.1 ml of 5-methylfuran-3-aldehyde 0.06 ml of acetic acid and 318 mg of sodium triacetoxyborohydride were added at room temperature, followed by stirring for 12 hours. To the reaction mixture, saturated aqueous sodium bicarbonate solution was added and the mixture was extracted with ethyl acetate. The organic layer was washed with brine and dried over anhydrous magnesium sulfate. After distilling the solvent off under reduced pressure, the residue was recrystallized from ethyl acetate/n-hexane to provide 198 mg of the title compound.

Step 2. Synthesis of (2R)-N-[1-(5-methyl-2-furylmethyl)piperidin-4-yl]-2-[(1R)-3,3-difluorocyclopentyl]-2-hydroxy-2-phenylacetamide To 88 mg of the 4-(tert-butyloxycarbonylamino)-1-(5-methyl-2-furylmethyl)piperidine as obtained in above step 1, 2 ml of 10% hydrogenchloride solution in methanol was added at room temperature, followed by stirring for about 12 hours. The solvent was distilled off under reduced pressure, and to a solution of the resultant residue in 4 ml of chloroform, 59 mg of (2R)-2-[(1R)-3,3-difluorocyclopentyl]-2-hydroxy-2-phenylacetic acid, 93 mg of hydroxybenzotriazole, 0.2 ml of triethylamine and 6 mg of 1-ethyl-3-(3-dimethylaminopropyl)carbodimide were added sequentially at room temperature, followed by stirring for 2 hours. After addition of water, the reaction mixture was extracted with chloroform. The organic layer was washed with brine and dried over anhydrous magnesium sulfate. Distilling the solvent off under reduced pressure, the residue was purified by silica gel column chromatography (developing solvent: chloroform/methanol=50/1) to provide 63 mg of the title compound as a white solid.

$^1$H-NMR (CDCl$_3$, δ ppm): 1.35–1.54 (2H, m), 1.60–2.25 (10H, m), 2.27 (3H, s), 2.71–2.86 (2H, m), 3.22–3.36 (1H, m), 3.40 (1H, s), 3.45 (2H, s), 3.60–3.76 (1H, m), 5.85–5.90 (1H, m), 6.05 (1H, d, J=3.0 Hz), 6.25 (1H, d, J=7.9 Hz), 7.26–7.40 (3H, m), 7.50–7.56 (2H, m)

low resolution FAB-MS (m/e, (C$_{24}$H$_{30}$F$_2$N$_2$O$_3$+H)$^+$): 433.

EXAMPLE 29

(2R)-N-[1-(3-methylbenzyl)piperidin-4-yl]-2-[(1R)-3,3-difluorocyclopentyl]-2-hydroxy-2-phenylacetamide Structural formula

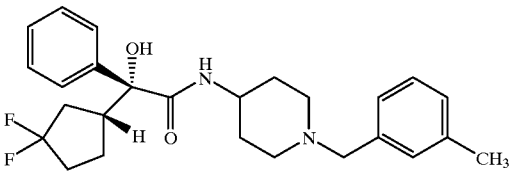

Step 1. Synthesis of 4-(tert-butyloxycarbonylamino)-1-(3-methylbenzyl)piperidine The title compound was prepared by a method similar to Example 15, using 4-(tert-butyloxycarbonylamino)piperidine and 3-methylbenzyl bromide.

Step 2. Synthesis of (2R)-N-[1-(3-methylbenzyl)piperidin-4-yl]-2-[(1R)-3,3-difluorocyclopentyl]-2-hydroxy-2-phenylacetamide The title compound was prepared by a method similar to Example 28, using the 4-(tert-butyloxycarbonylamino)-1-(3-methylbenzyl)piperidine as obtained in above step 1.

$^1$H-NMR (CDCl$_3$, δ ppm): 1.24–1.50 (2H, m), 1.50–2.25 (10H, m), 2.33 (3H, s), 2.60–2.82 (2H, m), 3.20–3.55 (3H, m), 3.42 (2H, s), 6.25 (1H, d, J=8.1 Hz), 7.00–7.14 (3H, m), 7.19 (1H, t, J=7.6 Hz), 7.23–7.42 (3H, m), 7.50–7.60 (2H, m)

low resolution FAB-MS (m/e, $(C_{26}H_{32}F_2N_2O_2+H)^+$) 443.

EXAMPLE 30

(2R)-N-[1-(4-methoxybenzyl)piperidin-4-yl]-2-[(1R)-3,3-difluorocyclopentyl]-2-hydroxy-2-phenylacetamide Structural formula

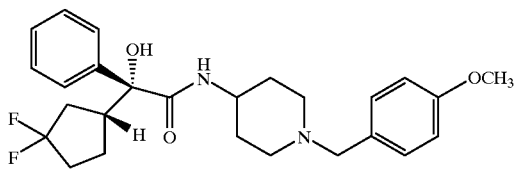

The title compound was prepared by a method similar to the step 2 of Example 10, using p-anisaldehyde.

$^1$H-NMR (CDCl$_3$, δ ppm): 1.32–1.47 (2H, m), 1.75–2.23 (10H, m), 2.65–2.76 (2H, m), 3.22–3.36 (1H, m), 3.42 (2H, s), 3.46 (1H, s), 3.63–3.76 (1H, m) 3.79 (3H, s), 6.27 (1H, d, J=8.2 Hz), 6.84 (2H, d, J=8.6 Hz), 7.19 (2H, d, J=8.6 Hz), 7.28–7.39 (3H, m), 7.52–7.56 (2H, m)

low resolution FAB-MS (m/e, $(C_{26}H_{32}F_2N_2O_3+H)^+$): 459.

EXAMPLE 31

(2R)-N-[1-(3-amino-5-methoxybenzyl)piperidin-4-yl]-2-[(1R)-3,3-difluorocyclopentyl]-2-hydroxy-2-phenylacetamide dihydrochloride Structural formula

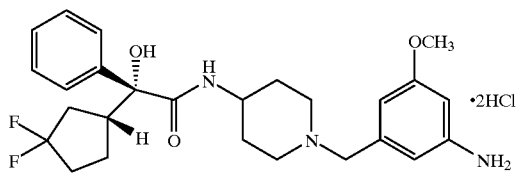

Step 1. Synthesis of methyl 3-tert-butoxycarbonylamino-5-methoxybenzoate

To a solution of 864 mg of methyl 3-methoxy-5-nitrobenzoate in 15 ml of methanol, 1.0 g of di-tert-butyl-dicarbonate and 912 mg of 10% palladium-on-carbon were added, followed by stirring for 7 hours at room temperature in a hydrogen atmosphere. The reaction liquid was filtered through Celite. Distilling the solvent off under reduced pressure, 1.28 g of the title compound was obtained as a white solid.

Step 2. Synthesis of 3-tert-butoxycarbonylamino-5-methoxybenzyl alcohol

To a solution of 1.28 mg of the methyl 3-tert-butoxycarbonylamino-5-methoxybenzoate as obtained in above step 1 in 8 ml of toluene, 12.1 ml of 1.0 M solution of diisobutylaluminum hydride in tetrahydrofuran was added at −78° C., followed by stirring for an hour at the same temperature. The reaction mixture was diluted with ethyl acetate, washed with water and then brine and dried over anhydrous magnesium sulfate. After distilling the solvent off under reduced pressure, the resulting residue was purified by silica gel column chromatography (developing solvent: hexane/ethyl acetate=7/3) to provide 262 mg of the title compound as an oil.

Step 3. Synthesis of 3-tert-butoxycarbonylamino-5-methoxybenzaldehyde

To a solution of 194 mg of the 3-tert-butoxycarbonylamino-5-methoxybenzyl alcohol as obtained in above step 2 in 10 ml of chloroform, 1.89 g of manganese dioxide was added at room temperature, followed by stirring for 2 hours. The reaction mixture was filtered through Celite. Distilling the solvent off under reduced pressure, 132 mg of the title compound was obtained as an oily substance.

Step 4. Synthesis of (2R)-N-[1-(3-amino-5-methoxybenzyl)piperidin-4-yl]-2-[(1R)-3,3-difluorocyclopentyl]-2-hydroxy-2-phenylacetamide dihydrochloride The title compound was prepared by a method similar to the step 2 of Example 10 and the step 6 of method 1 of Example 20, using the 3-tert-butoxycarbonylamino-5-methoxybenzaldehyde as obtained in above step 3.

$^1$H-NMR (CD$_3$OD, δ ppm): 1.74–2.14 (10H, m), 3.00–3.15 (2H, m), 3.27–3.52 (3H, m), 3.82–3.92 (1H, m), 3.89 (3H, s) 4.32 (2H, s), 7.01 (1H, s), 7.18–7.35 (5H, m), 7.56–7.60 (2H, m)

low resolution FAB-MS (m/e. $(C_{26}H_{33}F_2N_3O_3+H)^+$): 474.

EXAMPLE 32

(2R)-N-[1-(4-amino-3-fluorobenzyl)piperidin-4-yl]-2-[(1R)-3,3-difluorocyclopentyl]-2-hydroxy-2-phenylacetamide Structural formula

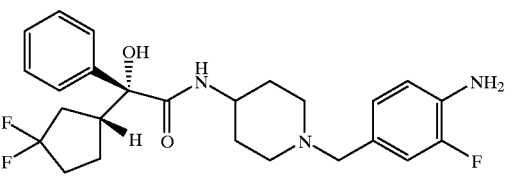

The title compound was prepared by a method similar to Example 22, using 3-fluoro-4-aminotoluene.

$^1$H-NMR (CDCl$_3$, δ ppm) 1.28–1.50 (2H, m), 1.50–2.32 (10H, m), 2.60–2.80 (2H, m), 3.20–3.38 (1H, m), 3.33 (2H, s), 3.45 (1H, s), 3.55–3.76 (3H, m), 6.25 (1H, d, J=8.2 Hz), 6.69 (1H, dd, J=8.1, 8.9 Hz), 6.82 (1H, dd, J=1.6, 8.1 Hz), 6.93 (1H, dd, J=1.6, 12.0 Hz), 7.24–7.40 (3H, m), 7.50–7.58 (2H, m)

low resolution FAB-MS (m/e, $(C_{25}H_{30}F_3N_3O_2+H)^+$): 462.

EXAMPLE 33

(2R)-N-[1-(6-amino-4-methylpyridin-2-yl)piperidin-4-yl]-2-[(1R)-3,3-difluorocyclopentyl]-2-hydroxy-2-phenylacetamide Structural formula

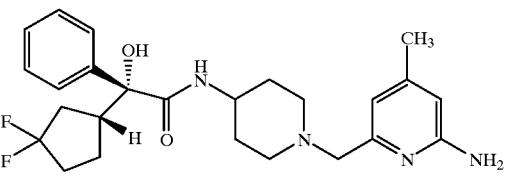

Step 1. Synthesis of 6-chloromethyl-4-methyl-2-acetylaminopyridine

To a solution of 23 mg of 6-acetylamino-4-methylpyridine-2-methanol in 2 ml of chloroform, 0.05 ml of thionyl chloride was added at room temperature, followed by heating for 15 minutes with stirring under reflux. Distilling the solvent off under reduced pressure, the title compound was obtained.

Step 2. Synthesis of (2R)-N-[1-(6-acetylamino-4-methylpyridin-2-yl)piperidin-4-yl]-2-[(1R)-3,3-difluorocyclopentyl]-2-hydroxy-2-phenylacetamide The title compound was prepared by a method similar to Example 15, using the 6-chloromethyl-4-methyl-2-acetylaminopyridine as obtained in above step 1.

Step 3. Synthesis of (2R)-N-[1-(6-amino-4-methylpyridin-2-yl)piperidin-4-yl]-2-[(1R)-3,3-difluorocyclopentyl]-2-hydroxy-2-phenylacetamide To a solution of 16.5 mg of the (2R)-N-[1-(6-acetylamino-4-methylpyridin-2-yl)piperidin-4-yl]-2-[(1R)-3,3-difluorocyclopentyl]-2-hydroxy-2-phenylacetamide as obtained in above step 2 in 1 ml of methanol, 0.5 ml of 3M aqueous sodium hydroxide solution was added, and stirred for 1.5 hours at 60° C. The reaction liquid was diluted with diethyl ether, washed with water and brine by the order stated and dried over anhydrous magnesium sulfate. Distilling the solvent off under reduced pressure, the resulting residue was purified by preparative thin-layer chromatography [Kieselgel™ 60F$_{254}$, Art 5744 (Merck); developing solvent: chloroform/methanol=10/1) to provide 14 mg of the title compound as an oily substance.

$^1$H-NMR (CDCl$_3$, δ ppm) 1.30–1.50 (2H, m), 1.71–2.30 (10H, m), 2.33 (3H, s), 2.62–2.76 (2H, m), 3.21–3.38 (1H, m), 3.29 (2H, s), 3.60–3.78 (1H, m), 4.35–4.51 (2H, m), 6.26 (1H, s), 6.35 (1H, d, J=8.1 Hz), 6.45 (1H, s), 7.25–7.40 (3H, m), 7.52–7.60 (2H, m)

low resolution FAB-MS (m/e, (C$_{25}$H$_{32}$F$_2$N$_4$O$_2$+H)$^+$) 459.

EXAMPLE 34

(2R)-N-[1-(3-amino-4-fluorobenzyl)piperidin-4-yl]-2-[(1R)-3,3-difluorocyclopentyl]-2-hydroxy-2-phenylacetamide dihydrochloride Structural formula

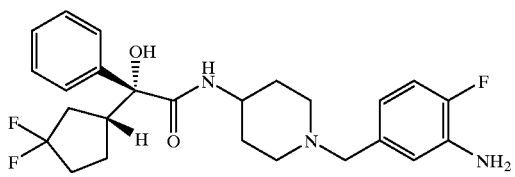

The title compound was prepared by a method similar to Example 22, using 2-fluoro-5-methylaniline.

$^1$H-NMR (CD$_3$OD, δ ppm) 1.68–2.11 (10H, m), 3.00–3.50 (5H, m), 3.79–3.90 (1H, m), 4.32 (2H, s), 7.18–7.30 (3H, m), 7.43 (1H, d, J=8.4 Hz), 7.52–7.56 (2H, m), 7.57–7.65 (1H, m), 7.73–7.78 (1H, m)

low resolution FAB-MS (m/e, (C$_{25}$H$_{30}$F$_3$N$_3$O$_2$+H)$^+$): 462.

EXAMPLE 35

(2R)-N-[1-(5-amino-2-fluorobenzyl)piperidin-4-yl]-2-[(1R)-3,3-difluorocyclopentyl]-2-hydroxy-2-phenylacetamide Structural formula

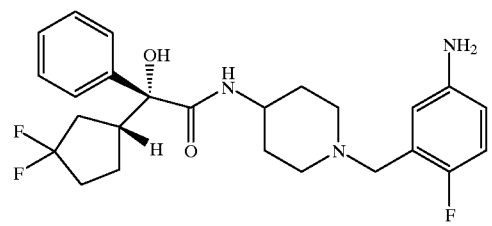

The title compound was prepared by a method similar to the step 2 of Example 22 and Example 23, using 2-fluoro-5-nitrotoluene.

$^1$H-NMR (CDCl$_3$, δ ppm) 1.36–1.49 (2H, m), 1.57–2.26 (10H, m), 2.71–2.78 (2H, m), 3.24–3.36 (1H, m), 3.42–3.57 (5H, m), 3.66–3.75 (1H, m), 6.24 (1H, d, J=8.1 Hz), 6.51–6.56 (1H, m), 6.65–6.68 (1H, m), 6.82 (1H, t, J=9.0 Hz), 7.29–7.40 (3H, m) 7.53–7.57 (2H, m)

low resolution FAB-MS (m/e, (C$_{25}$H$_{30}$F$_3$N$_3$O$_2$+H)$^+$): 462.

EXAMPLE 36

(2R)-N-[1-(2-amino-4-chloropyridin-6-ylmethyl)piperidin-4-yl]-2-[(1R)-3,3-difluorocyclopentyl]-2-hydroxy-2-phenylacetamide Structural formula

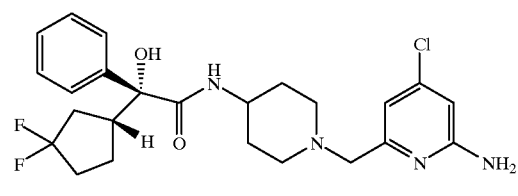

The title compound was prepared by a method similar to method 2 of Example 20, using methyl 4-chloro-6-hydroxymethylpyridine-2-carboxylate.

$^1$H-NMR (CDCl$_3$, δ ppm): 1.42–1.54 (2H, m), 1.78–2.26 (10H, m), 2.76–2.79 (2H, m), 3.28–3.38 (1H, m), 3.42–3.47 (3H, m), 3.67–3.75 (1H, m), 4.53–4.56 (2H, m), 6.36 (1H, d, J=7.2 Hz), 6.38 (1H, d, J=1.6 Hz), 6.72 (1H, d, J=1.6 Hz), 7.25–7.39 (3H, m), 7.53–7.57 (2H, m)

low resolution FAB-MS (m/e, (C$_{24}$H$_{29}$ClF$_2$N$_4$O$_2$+H)$^+$): 479.

EXAMPLE 37

(2R)-N-[1-(3-amino-5-chlorobenzyl)piperidin-4-yl]-2-[(1R)-3,3-difluorocyclopentyl]-2-hydroxy-2-phenylacetamide Structural formula

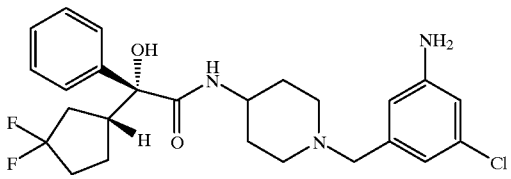

Step 1. Synthesis of 3-chloro-5-nitrobenzyl methanesulfonate

To a solution of 92 mg of 3-chloro-5-nitrobenzyl alcohol in 3 ml of chloroform, 0.3 ml of triethylamine and 0.1 ml of methanesulfonyl chloride were added at room temperature, followed by stirring for 40 minutes, addition of saturated aqueous sodium bicarbonate solution and further stirring for 30 minutes. The reaction mixture was diluted with diethyl ether, washed with saturated aqueous sodium bicarbonate solution and then brine and dried over anhydrous magnesium sulfate. Distilling the solvent off under reduced pressure, 119 mg of the title compound was obtained as an oil.

Step 2. Synthesis of (2R)-N-[1-(3-amino-5-chlorobenzyl)piperidin-4-yl]-2-[(1R)-3,3-difluorocyclopentyl]-2-hydroxy-2-phenylacetamide The title compound was obtained by a method similar to Example 23, using the 3-chloro-5-nitrobenzyl methanesulfonate as obtained in above step 1.

$^1$H-NMR (CDCl$_3$, δ ppm): 1.30–1.44 (2H, m), 1.73–2.22 (10H, m), 2.68–2.73 (2H, m), 3.24–3.36 (1H, m), 3.32 (2H, s), 3.44 (1H, brs), 3.61–3.77 (3H, m), 6.28 (1H, d, J=8.4 Hz), 6.49 (1H, d, J=1.9 Hz), 6.55 (1H, dd, J=1.7, 1.9 Hz), 6.66 (1H, d, J=1.7 Hz), 7.29–7.39 (3H, m), 7.53–7.56 (2H, m)

low resolution FAB-MS (m/e, (C$_{25}$H$_{30}$ClF$_2$N$_3$O$_2$+H)$^+$): 459.

EXAMPLE 38

(2R)-N-[1-(4-amino-3,5-difluorobenzyl)piperidin-4-yl]-2-[(1R)-3,3-difluorocyclopentyl]-2-hydroxy-2-phenylacetamide Structural formula

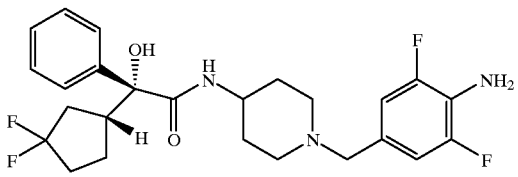

The title compound was prepared by a method similar to the step 2 of Example 10, using 4-amino-3,5-difluorobenzaldehyde.

$^1$H-NMR (CDCl$_3$, δ ppm): 1.24–2.22 (12H, m), 2.66–2.72 (2H, m), 3.27–3.41 (4H, m), 3.66–3.71 (3H, m), 6.28 (1H, d, J=7.8 Hz), 6.77 (2H, d, J=8.3 Hz), 7.28–7.39 (3H, m), 7.54–7.56 (2H, m)

low resolution FAB-MS (m/e, (C$_{25}$H$_{29}$F$_4$N$_3$O$_2$+H)$^+$) 480.

EXAMPLE 39

(2R)-N-[1-(benzimidazol-5-ylmethyl)piperidin-4-yl]-2-[(1R)-3,3-difluorocyclopentyl]-2-hydroxy-2-phenylacetamide Structural formula

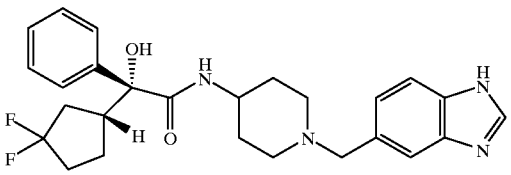

The title compound was prepared by a method similar to the step 2 of Example 10, using benzimidazole-5-carbaldehyde.

$^1$H-NMR (CD$_3$OD, δ ppm): 1.45–2.25 (10H, m), 2.25–2.48 (2H, m), 2.90–3.10 (2H, m), 3.20–3.42 (1H, m), 3.56–3.75 (1H, m), 3.82 (2H, s), 7.18–7.40 (4H, m), 7.51–7.75 (4H, m), 8.17 (1H, s)

low resolution FAB-MS (m/e, (C$_{26}$H$_{30}$F$_2$N$_4$O$_2$+H)$^+$): 469.

EXAMPLE 40

(2R)-N-[1-(6-aminopyridin-2-ylmethyl)piperidin-4-yl]-2-(3,3-difluorocyclobutyl)-2-hydroxy-2-phenylacetamide Structural formula

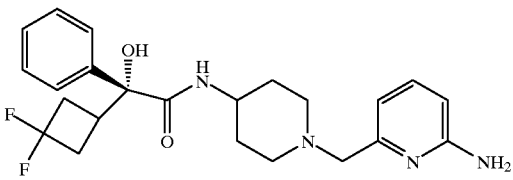

The title compound was prepared by a method similar to the step 4 of method 2 of Example 20, using (2R)-(3,3-difluorocyclobutyl)-2-hydroxyphenylacetic acid and 4-amino-1-(6-aminopyridin-2-ylmethyl)piperidine trihydrochloride.

$^1$H-NMR (CDCl$_3$, δ ppm): 1.20–1.52 (2H, m), 1.60–1.86 (2H, m), 2.08–2.22 (2H, m), 2.40–2.82 (6H, m), 3.07–3.21 (1H, m), 3.41 (2H, s), 3.60–3.80 (1H, m), 3.84 (1H, brs), 4.40 (2H, brs), 6.01 (1H, d, J=8.1 Hz), 6.36 (1H, d, J=8.2 Hz), 6.66 (1H, d, J=8.2 Hz), 7.28–7.42 (4H, m), 7.43–7.50 (2H, m)

low resolution FAB-MS (m/e, (C$_{23}$H$_{28}$F$_2$N$_4$O$_2$+H)$^+$) 431.

EXAMPLE 41

(2R)-N-[1-(6-aminopyridin-2-ylmethyl)piperidin-4-yl]-2-(4,4-difluorocyclohexyl)-2-hydroxy-2-phenylacetamide Structural formula

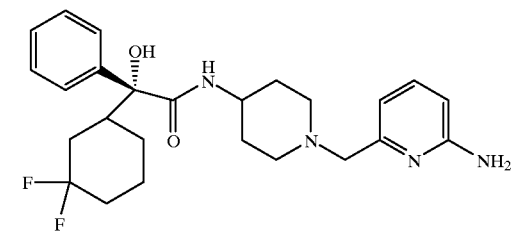

The title compound was prepared by a method similar to the step 4 of method 2 of Example 20, using (2R)-(4,4- difluorocyclohexyl)-2-hydroxyphenylacetic acid and 4-amino-1-(6-aminopyridin-2-ylmethyl)piperidine trihydrochloride.

¹H-NMR (CDCl₃, δ ppm): 1.20–1.97 (10H, m), 1.97–2.22 (4H, m), 2.44–2.68 (1H, m), 2.70–2.92 (3H, m), 3.42 (2H, s), 3.62–3.80 (1H, m), 4.42 (2H, brs), 6.36 (1H, d, J=8.2 Hz), 6.62 (1H, d, J=7.9 Hz), 6.67 (1H, d, J=8.2 Hz), 7.24–7.42 (4H, m), 7.55–7.62 (2H, m)

low resolution FAB-MS (m/e, (C₂₅H₃₂F₂N₄O₂+H)⁺): 459.

EXAMPLE 42

(2R)-N-[1-(6-aminopyridin-2-ylmethyl)piperidin-4-yl]-2-[(1R)-(3,3-difluorocyclopentyl)-2-(4-fluorophenyl)-2-hydroxyacetamide Structural formula

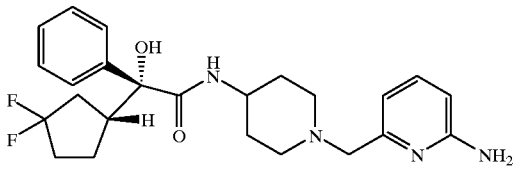

The title compound was prepared by a method similar to the method 1 of Example 20, using (2R)-(3,3-difluorocyclopentyl)-2-(4-fluorophenyl)-2-hydroxyacetic acid.

¹H-NMR (CDCl₃, δ ppm): 1.39–1.55 (2H, m), 1.70–2.22 (10H, m), 2.73–2.81 (2H, m), 3.23–3.36 (1H, m), 3.43 (2H, s), 3.65–3.77 (1H, m), 4.43 (2H, brs), 6.31 (1H, d, J=7.6 Hz), 6.37 (1H, d, J=8.2 Hz) 6.67 (1H, d, J=7.4 Hz), 7.01–7.08 (2H, m), 7.37 (1H, dd, J=7.4, 8.2 Hz), 7.51–7.58 (2H, m)

low resolution FAB-MS (m/e, (C₂₄H₂₉F₃N₄O₂+H)⁺): 463.

REFERENTIAL EXAMPLE 1

(2R)-[(1R)-3-oxocyclopentyl]-2-hydroxy-2-phenylacetic acid

Step 1. Synthesis of (2R,5R)-2-(t-butyl)-5-[(1R)-3-oxocyclopentyl]-5-phenyl-1,3-dioxolan-4-one and (2R,5R)-2-(t-butyl)-5-[(1S) -3-oxocyclopentyl]-5-phenyl-1,3-dioxolan-4-one To a mixture of 510 mg of (2R,5R)-2-(t-butyl)-5-phenyl-1,3-dioxolan-4-one-which had been synthesized by the method of D. Seebach, et al. [Tetrahedron. Vol. 40, pp. 1313–1324 (1984)] in 20 ml of tetrahydrofuran and 1 ml of hexamethylphosphoric triamide, 1.7 ml of 1.5M lithium diisopropylamide solution in hexane was added dropwise at −78° C., followed by stirring for 30 minutes. Then a solution of 285 mg of cyclopentenone in 1.5 ml of tetrahydrofuran was added, and the reaction mixture was stirred for 1.5 hours. The reaction mixture was diluted with ethyl acetate, washed with saturated aqueous ammonium chloride solution, water and then brine, and dried over anhydrous magnesium sulfate. Distilling the solvent off under reduced pressure, resulting residue was purified by medium pressure silica gel column chromatography (developing solvent: hexane/ethyl acetate=15/1–10/1). Thus 150 mg and 254 mg, respectively, of the title compounds were obtained as oil. Configuration of each of the compounds was determined from NOE of NMR.

Step 2. Synthesis of (2R)-[(1R)-3-oxocyclopentyl]-2-hydroxy-2-phenylacetic acid

To a solution of 61 mg of (2R,5R)-2-(t-butyl)-5-[(1R)-3-oxocyclopentyl]-5-phenyl-1,3-dioxolan-4-one in 3 ml of methanol, 1 ml of 1N aqueous sodium hydroxide solution was added, followed by stirring for 3 hours at room temperature. Distilling the methanol off under reduced pressure, the residue was diluted with water and washed with diethyl ether. The aqueous layer was made acidic with 1N hydrochloric acid and extracted with diethyl ether. The organic layer was dried over anhydrous magnesium sulfate to provide 48 mg of the title compound.

REFERENTIAL EXAMPLE 2

(2R)-[(1S)-3-oxocyclopentyl]-2-hydroxy-2-phenylacetic acid

The title compound was prepared by a method similar to the step 2 of Referential Example 1, using (2R,5R)-2-(t-butyl)-5-[(1S)-3-oxocyclopentyl]-5-phenyl-1,3-dioxolan-4-one.

REFERENTIAL EXAMPLE 3

(2R)-[(1R)-3,3-difluorocyclopentyl]-2-hydroxy-2-phenylacetic acid

Step 1. Synthesis of (2R,5R)-2-(t-butyl)-5-[(1R)-3,3-difluorocyclopentyl]-5-phenyl-1,3-dioxolan-4-one To a solution of 256 mg of (2R,5R)-2-(t-butyl)-5-[(1R)-3-oxocyclopentyl]-5-phenyl-1,3-dioxolan-4-one in 3 ml of chloroform, 0.34 ml of diethylaminosulfurtrifluoride was added under cooling with ice, followed by stirring for 20 hours at room temperature. The reaction mixture was diluted with diethyl ether, washed with water and then brine, and dried over anhydrous magnesium sulfate. Distilling the solvent off under reduced pressure, resulting residue was purified by silica gel column chromatography (developing solvent: hexane/ethyl acetate=20/1) to provide 115 mg of the title compound.

Step 2. Synthesis of (2R)-[(1R)-3,3-difluorocyclopentyl]-2-hydroxy-2-phenylacetic acid The title compound was prepared by a method similar to the step 2 of Referential Example 1, using (2R,5R)-2-(t-butyl)-5-[(1R)-3,3-difluorocyclopentyl]-5-phenyl-1,3-dioxolan-4-one.

REFERENTIAL EXAMPLE 4

(2R)-[(1S)-3,3-difluorocyclopentyl]-2-hydroxy-2-phenylacetic acid

The title compound was prepared by a method similar to Referential Example 3, using (2R,5R)-2-(t-butyl)-5-[(1S)-3-oxocyclopentyl]-5-phenyl-1,3-dioxolan-4-one.

REFERENTIAL EXAMPLE 5

(2R)-[(1S)-3-hydroxycyclopentyl]-2-hydroxy-2-phenylacetic acid

Step 1. Synthesis of (2R,5R)-2-(t-butyl)-5-[(1S)-3-hydroxycyclopentyl]-5-phenyl-1,3-dioxolan-4-one To a solution of 169 mg of (2R,5R)-2-(t-butyl)-5-[(1S)-3-oxocyclopentyl]-5-phenyl-1,3-dioxolan-4-one in 2 ml of methanol, 71 mg of sodium borohydride was added under cooling with ice, followed by stirring for 30 minutes at the same temperature. The reaction mixture was diluted with diethyl ether, washed with water and then brine, and dried over anhydrous magnesium sulfate. Distilling the solvent off under reduced pressure, 157 mg of the title compound was obtained as a colorless oil.

Step 2. Synthesis of (2R)-[(1S)-3-hydroxycyclopentyl]-2-hydroxy-2-phenylacetic acid The title compound was prepared by a method similar to the step 2 of Referential Example 1, using (2R,5R)-2-(t-butyl)-5-[(1S)-3-hydroxycyclopentyl]-5-phenyl-1,3-dioxolan-4-one.

REFERENTIAL EXAMPLE 6

(2R)-[(1R)-3-hydroxycylopentyl]-2-hydroxy-2-phenylacetic acid

The title compound was prepared by a method similar to Referential Example 5, using (2R,5R)-2-(t-butyl)-5-[(1R)-3-oxocyclopentyl]-5-phenyl-1,3-dioxolan-4-one.

REFERENTIAL EXAMPLE 7

(2R)-[(1S)-3-fluorocyclopentyl]-2-hydroxy-2-phenylacetic acid

The title compound was prepared by a method similar to Referential Example 3, using (2R)-[(1S)-3-hydroxycyclopentyl]-2-hydroxy-2-phenylacetic acid.

REFERENTIAL EXAMPLE 8

(2R)-[(1R)-3-fluorocyclopentyl]-2-hydroxy-2-phenylacetic acid

The title compound was prepared by a method similar to Referential Example 3, using (2R)-[(1R)-3-hydroxycyclopentyl]-2-hydroxy-2-phenylacetic acid.

REFERENTIAL EXAMPLE 9

2-cyclopentyl-2-hydroxy-2-phenylacetic acid

To a solution of 23.5 g of ethyl phenylglyoxylate in 200 ml of tetrahydrofuran, 70 ml of 2.0 M cyclopentylmagnesium chloride solution in diethyl ether was added dropwise under cooling with ice, followed by stirring for 30 minutes at the same temperature. The reaction mixture was diluted with ethyl acetate, washed with saturated aqueous ammonium chloride solution and brine, and dried over anhydrous magnesium sulfate. Distilling the solvent off under reduced pressure, the residue was purified by silica gel column chromatography (developing solvent: hexane/ethyl acetate= 30/1–20/1) to provide 11 g of ethyl 2-cyclopentyl-2-hydroxy-2-phenylacetate, which was dissolved in 40 ml of methanol. To the solution 20 ml of 4N aqueous sodium hydroxide solution was added at room temperature, followed by stirring for 2 hours at the same temperature and further for 1 hour at 50° C. Distilling the methanol off under reduced pressure, the aqueous layer was made weakly acidic with 4N hydrochloric acid and extracted with ethyl acetate. The organic layer was washed with water and then brine and dried over anhydrous magnesium sulfate. Distilling the solvent off under reduced pressure, the residue was washed with 1:1 mixture of diethyl ether and hexane. Thus, 8.7 g of the title compound was obtained.

REFERENTIAL EXAMPLE 10

(2R)-[(1R)-3,3-difluorocyclopentyl]-2-hydroxy-2-phenylacetic acid

Step 1. Synthesis of (2R,5R)-2-(t-butyl)-5-[(1S,2R,5R,6S,7R)-3-oxotricyclo[5.2.1.0$^{2,6}$]dec-8-en-5-yl]-5-phenyl-1,3-dioxolan-4-one To a solution of 32 g of (2R,5R)-2-(t-butyl)-5-phenyl-1,3-dioxolan-4-one in 1.1 l of tetrahydrofuran, 105 ml of 1.5 M lithium diisopropylamide solution in hexane was added dropwise at −78° C., followed by stirring for 30 minutes, addition of 23.4 g of (1S,2R,6S,7R)-tricyclo[5.2.1.0$^{2,6}$]dec-4,8-dien-3-one as dissolved in 300 ml of tetrahydrofuran, and further stirring for 1.5 hours. The reaction mixture was diluted with ethyl acetate, washed with saturated aqueous ammonium chloride solution, water and then brine, and dried over anhydrous magnesium sulfate. Distilling the solvent off under reduced pressure, the residue was recrystallized from hexane-ethyl acetate. Thus 36.9 g of the title compound was obtained as a white solid.

Step 2. Synthesis of (2R,5R)-2-(t-butyl)-5-[(1S)-4-oxo-2-cyclopentenyl]-5-phenyl-1,3-dioxolan-4-one A solution of 25.6 g of the (2R,5R)-2-(t-butyl)-5-[(1S,2R,5R,6S,7R)-3-oxo-8-tricyclo [5.2.1.0$^{2,6}$]-dec-8-en-5-yl]-5-phenyl-1,3-dioxolan-4-one as obtained in above step 1 in 350 ml of 1,2-dichlorobenzene was heated at 175° C. for 7 hours with stirring, under nitrogen atmosphere. Thus precipitated solid was recovered by filtration and washed with hexane to provide 14 g of the title compound as a white solid.

Step 3. Synthesis of (2R,5R)-2-(t-butyl)-5-[(1R)-3-oxocyclopentyl]-5-phenyl-1,3-dioxolan-4-one To a solution of 19.1 g of the (2R,5R)-2-(t-butyl)- 5-[(1S)-4-oxo-2-cyclopentenyl]-5-phenyl-1,3-dioxolan-4-one as obtained in above step 2 in 700 ml of ethyl acetate, 2.0 g of 10% palladium-on-carbon was added, followed by stirring for 2 hours at room temperature under hydrogen atmosphere. Filtering the catalyst off then distilling the solvent off under reduced pressure, the residue was recrystallized from hexane-ethyl acetate to provide 14 g of the title compound as a white solid.

Step 4. Synthesis of (2R)-[(1R)-3,3-difluorocyclopentyl]-2-hydroxy-2-phenylacetic acid The title compound was prepared by a method similar to Referential Example 3, using the (2R,5R)-2-(t-butyl)-5-[(1R)-3-oxocyclopentyl]-5-phenyl-1,3-dioxolan-4-one as obtained in above step 3.

REFERENTIAL EXAMPLE 11

(2R)-(3,3-difluorocyclopentyl)-2-(4-fluorophenyl)-2-hydroxyacetic acid

The title compound was prepared by a method similar to the step 1 of Referential Example 1 and Referential Example 3, using (R)-4-fluoromandelic acid.

REFERENTIAL EXAMPLE 12

(2R)-(3,3-difluorocyclobutyl)-2-hydroxy-2-phenylacetic acid

Step 1. Synthesis of (2R,5R)-2-(t-butyl)-5-(3-benzyloxy-1-hydroxycyclobutyl)-5-phenyl-1,3-dioxolan-4-one The title compound was prepared by a method similar to the step 1 of Referential Example 1, using 3-benzyloxycyclobutanone.

Step 2. Synthesis of (2R,5R)-2-(t-butyl)-5-(3-benzyloxycyclobutyl)-5-phenyl-1,3-dioxolan-4-one To a solution of 2.82 g of the (2R,5R)-2-(t-butyl)-5-(3-benzyloxy-1-hydroxycyclobutyl)-5-phenyl-1,3-dioxolan-4-one as obtained in above step 1 in 80 ml of chloroform, 2.6 g of 4-dimethylaminopyridine was added under cooling with ice, followed by stirring for an hour at the same temperature. To the reaction mixture, 1 ml of methyl chloroglyoxylate was added, followed by stirring for an hour. The reaction mixture was diluted with chloroform, washed with water and then brine, and dried over anhydrous magnesium sulfate. Distilling the solvent off under reduced pressure, the residue was mixed with hexane/ethyl acetate=1/1 liquid mixture and filtered through a silica gel column. Distilling the solvent off under reduced pressure, the residue was dissolved in 80 ml of toluene, and to the solution 56 mg of 2,2'-azobis(isobutyronitrile) and 2.3 ml of tri-n-butyltin hydride were added, followed by heating for 4 hours at 110° C. with stirring. Distilling the solvent off under reduced pressure, the residue was purified by silica gel column chromatography (developing solvent: hexane/ethyl acetate= 8/1) to provide 1.82 g of the title compound as an oily substance.

Step 3. Synthesis of (2R,5R)-2-(t-butyl)-5-(3-oxocyclobutyl)-5-phenyl-1,3-dioxolan-4-one To a solution of 1.82 g of the (2R,5R)-2-(t-butyl)-5-(3-benzyloxycyclobutyl)-5-phenyl-1,3-dioxolan-4-one as obtained in above step 2 in 40 ml of ethanol. 430 mg of palladium hydroxide-carbon was added, followed by stirring for 6 hours at room temperature under hydrogen atmosphere. The reaction mixture was filtered through Celite. Distilling the solvent off under reduced pressure, the residue was dissolved in 5 ml of dichloromethane, and the resulting solution was added dropwise at −78° C. to a reaction mixture formed by adding 0.63 ml of oxalyl chloride to 1.1 ml of dimethylsulfoxide in 50 ml of dichloromethane at −78° C. and stirring for 5 minutes. After stirring for 15 minutes at the same temperature, 0.5 ml of triethylamine was added to the reaction mixture and stirred for 30 minutes while raising the temperature to room temperature. The reaction liquid was diluted with chloroform, washed with water and then brine, and dried over anhydrous magnesium sulfate. Distilling the solvent off under reduced pressure, the residue was purified by silica gel column chromatography (developing solvent: hexane/ethyl acetate=8/1) to provide 1.36 g of the title compound as an oily substance.

Step 4. Synthesis of (2R)-(3,3-difluorocyclobutyl)-2-hydroxy-2-phenylacetic acid The title compound was prepared by a method similar to Referential Example 3, using the (2R,5R)-2-(t-butyl)-5-(3-oxocyclobutyl)-5-phenyl-1,3-dioxolan-4-one as obtained in above step 3.

REFERENTIAL EXAMPLE 13

(2R)-(4,4-difluorocyclohexyl)-2-hydroxy-2-phenylacetic acid

Step 1. Synthesis of (2R,5R)-2-(t-butyl)-5-(1,4-dioxaspiro[4.5]-dec-8-yl)-5-phenyl-1,3-dioxolan-4-one The title compound was prepared by a method similar to the steps 1 and 2 of Referential Example 12, using 1,4-dioxa-8-oxospiro[4.5]decane.

Step 2. Synthesis of (2R,5R)-2-(t-butyl)-5-(4-oxocyclohexyl)-5-phenyl-1,3-dioxolan-4-one To a solution of 83 mg of the (2R,5R)-2-(t-butyl)-5-(1,4-dioxaspiro[4.5]dec-8-yl)-5-phenyl-1,3-dioxolan-4-one in a mixture of 4 ml of acetone and 0.4 ml of water, 52 mg of p-toluenesulfonic acid was added at room temperature, followed by stirring for 13 hours at 50° C. Distilling the acetone off under reduced pressure, the residue was diluted with ethyl acetate, washed with saturated aqueous sodium bicarbonate solution and then brine, and dried over anhydrous magnesium sulfate. Distilling the solvent off under reduced pressure, 70 mg of the title compound was obtained as an oil.

Step 3. Synthesis of (2R)-(4,4-difluorocyclohexyl)-2-hydroxyphenylacetic acid

The title compound was prepared by a method similar to Referential Example 3, using the (2R,5R)-2-(t-butyl)-5-(4-oxocyclohexyl)-5-phenyl-1,3-dioxolan-4-one.

REFERENTIAL EXAMPLE 14

(2R)-[(1R)-3,3-difluorocyclopentyl]-2-hydroxy-2-phenylacetic acid

Step 1. Synthesis of (2R,5R)-2-(t-butyl)-5-[(1R)-3-hydroxyiminocyclopentyl]-5-phenyl-1,3-dioxolan-4-one To a solution of 46 mg of (2R,5R)-2-(t-butyl)-5-[(1R)-3-oxocyclopentyl]-5-phenyl-1,3-dioxolan-4-one in 1.5 ml of pyridine, 85 mg of hydroxylamine hydrochloride was added and the mixture was stirred for 1 hour at room temperature. The reaction mixture was diluted with ethyl acetate and washed with water and brine, and then dried over anhydrous sodium sulfate. The solvent was removed under reduced pressure to give 55 mg of the title compound.

Step 2. Synthesis of (2R,5R)-2-(t-butyl)-5-[(1R)-3,3-difluorocyclopentyl]-5-phenyl-1,3-dioxolan-4-one To a mixture of 20 mg of nitrosonium tetrafluoro borate and 0.5 ml of 70% hydrogen fluoride-pyridine, a solution of 34 mg of (2R,5R)-2-(t-butyl)-5-[(1R)-3-hydroxyiminocyclopentyl]-5-phenyl-1,3-dioxolan-4-one in 0.5 ml of dichloromethane was added under ice-cooling. The mixture was stirred for 10 minutes at 0° C. and 5 hours at room temperature. Water was added to the reaction mixture under ice-cooling and the mixture was extracted with ethyl acetate. The organic layer was washed with saturated aqueous sodium bicarbonate solution and then brine, and dried over anhydrous magnesium sulfate. The solvent was removed under reduced pressure to give 35 mg of the title compound.

Step 3. (2R)-[(1R)-3,3-difluorocyclopentyl]-2-hydroxy-2-phenylacetic acid

The title compound was prepared by a method similar to the step 2 of Referential Example 1, using (2R,5R)-2-(t-butyl)-5-[(1R)-3,3-difluorocyclopentyl]-5-phenyl-1,3-dioxolan-4-one.

Industrially utilizability

The fluorine-containing 1,4-disubstituted piperidine derivatives of the present invention have not only potent selective antagonistic activity for muscarinic $M_3$ receptors but also little side effect. Furthermore they exhibit excellent oral activity, duration of action and pharmacokinetics. Hence, they are very useful in the treatment or prophylaxis of diseases such respiratory diseases as chronic obstructive pulmonary diseases, chronic bronchitis, asthma and rhinitis: digestive diseases such as irritable bowel syndrome, convulsive colitis, diverticulitis and pain accompanying contraction of smooth muscles of the digestive system: urinary disorders like urinary incontinence and frequency in neurogenic pollakiurea, neurogenic bladder, nocturnal enuresis, unstable bladder, cystospasm and chronic cystisis: and motion sickness.

We claim:

1. 4-Amino-1-(6-aminopyridin-2-ylmethyl) piperidine or a salt thereof.

2. The compound according to claim 1 wherein the salt is trihydrochloride.

* * * * *